(12) United States Patent
Muccio et al.

(10) Patent No.: US 10,800,726 B2
(45) Date of Patent: Oct. 13, 2020

(54) REXINOID COMPOUNDS AND METHODS OF USING REXINOID COMPOUNDS FOR TREATING METABOLIC DISORDERS AND CANCER

(71) Applicant: THE UAB RESEARCH FOUNDATION, Birmingham, AL (US)

(72) Inventors: Donald D. Muccio, Hoover, AL (US); Venkatram Reddy Atigadda, Birmingham, AL (US); Wayne J. Brouillette, Pelham, AL (US); Clinton J. Grubbs, Pelham, AL (US); Jeonga Kim, Hoover, AL (US)

(73) Assignee: THE UAB RESEARCH FOUNDATION, Birmingham, AL (US)

( * ) Notice: Subject to any disclaimer, the term of this patent is extended or adjusted under 35 U.S.C. 154(b) by 0 days.

(21) Appl. No.: 15/322,803

(22) PCT Filed: Jun. 30, 2015

(86) PCT No.: PCT/US2015/038596
§ 371 (c)(1),
(2) Date: Dec. 29, 2016

(87) PCT Pub. No.: WO2016/004066
PCT Pub. Date: Jan. 7, 2016

(65) Prior Publication Data
US 2018/0201565 A1    Jul. 19, 2018

Related U.S. Application Data

(60) Provisional application No. 62/019,170, filed on Jun. 30, 2014.

(51) Int. Cl.
| | |
|---|---|
| *C07C 57/42* | (2006.01) |
| *C07C 57/40* | (2006.01) |
| *C07C 63/331* | (2006.01) |
| *C07C 57/60* | (2006.01) |
| *A61P 35/00* | (2006.01) |
| *C07C 57/62* | (2006.01) |
| *A61K 45/06* | (2006.01) |
| *C07D 307/54* | (2006.01) |
| *C07C 59/56* | (2006.01) |
| *A61P 3/04* | (2006.01) |
| *A61P 3/06* | (2006.01) |
| *A61P 3/10* | (2006.01) |

(52) U.S. Cl.
CPC .............. *C07C 57/42* (2013.01); *A61K 45/06* (2013.01); *A61P 3/04* (2018.01); *A61P 3/06* (2018.01); *A61P 3/10* (2018.01); *A61P 35/00* (2018.01); *C07C 57/40* (2013.01); *C07C 57/60* (2013.01); *C07C 57/62* (2013.01); *C07C 59/56* (2013.01); *C07C 63/331* (2013.01); *C07D 307/54* (2013.01); *C07C 2602/10* (2017.05)

(58) Field of Classification Search
CPC ........ C07C 57/42; C07C 63/331; C07C 57/40; C07C 57/60; A61P 35/00
See application file for complete search history.

(56) References Cited

U.S. PATENT DOCUMENTS

| 5,094,783 A | 3/1992 | Muccio et al. |
|---|---|---|
| 6,903,128 B2 * | 6/2005 | Duplantier ............ C07C 229/34 514/394 |
| 2004/0087590 A1 | 5/2004 | Makriyannis et al. |
| 2006/0111445 A1 | 5/2006 | Adje et al. |
| 2007/0155813 A1 | 7/2007 | Kitamura et al. |
| 2010/0204327 A1 | 8/2010 | Brouillette et al. |
| 2010/0210727 A1 | 8/2010 | Pace-Asciak et al. |
| 2013/0203754 A1 | 8/2013 | Yang et al. |

FOREIGN PATENT DOCUMENTS

WO   2006/057922 A2   6/2006

OTHER PUBLICATIONS

Petros et al., Discovery of a Potent Inhibitor of the Antiapoptotic Protein Bcl-xl from NMR and Parallel Synthesis. J. Med. Chem., vol. 49, pp. 656-663 (Year: 2006).*
Sun et al., "The ligand and base-free Pd-catalyzed oxidative Heck reaction of arylboronic acids and olefins." Orgainic & Biomolecular Chemistry, vol. 10(23), p. 4512-4515 (Year: 2012).*
Extended European Search Report issued for EP Application No. 15815081.3 dated Mar. 19, 2018 (15 pages).
Chen et al., "Phosphine-Free Palladium Catalytic System for the Selective Direct Arylation of Furans or Thiophenes bearing Alkenes and Inhibition of Heck-Type Reaction," Advanced Synthesis & Catalysis, vol. 353, No. 14-15, Oct. 1, 2011, pp. 2749-2760.
Joharapurkar et al., "Selective Thyromimetics Using Receptor and Tissue Selectivity Approaches: Prospects for Dyslipidemia," Journal of Medicinal Chemistry, vol. 55, No. 12, Jun. 28, 2012, pp. 5649-5675.
Liby et al., "Triterpenoids and rexinoids as multifunctional agents for the prevention and treatment of cancer," Nature Reviews Cancer, vol. 7, Apr. 19, 2007 (Apr. 19, 2007), pp. 357-369.
Pasto et al., "Silver ion-assisted solvolysis of phenacyl halides in aqueous ethanol", Journal of Organic Chemistry, vol. 32, No. 3, Mar. 1, 1967, pp. 778-781.

(Continued)

*Primary Examiner* — Barbara P Badio
(74) *Attorney, Agent, or Firm* — Kilpatrick Townsend & Stockton LLP

(57) ABSTRACT

Novel rexinoid compounds are provided herein. Also provided herein are methods of using the compounds to treat disorders, such as metabolic disorders, diabetes, insulin resistance, glucose intolerance, obesity, steatosis, inflammation, and/or cancer.

8 Claims, 4 Drawing Sheets

(56) References Cited

OTHER PUBLICATIONS

Wiesner et al., "Structure-Activity Relationships of Novel Anti-Malarial Agents. Part 4: N-(3-Benzoyl-4-tolulacetylaminophenyl)-3-(5-aryl-2-furyl)acrylic Acid Amides," Bioorganic & Medicinal Chemistry Letters, 12: 2681-2683 (2002).
Zhang et al., "Pd-Catalyzed Efficient One-Pot Sequential Cross-Coupling Reactions of Aryl Dihalides," Organic Letters, vol. 10, No. 17. Sep. 4, 2008, pp. 3849-3852.
Zhang et al., "Palladium/Imidazolium salt as a versatile catalyst for sequential coupling reactions of aryl dihalides to unsymmetrically substituted arenes," Tetrahedron, vol. 66, No. 6 (2010), pp. 1188-1195.
Zhao J et al., "Palladium-catalyzed alkenation of thiophenes and furans by regioselective C-H bond functionalization," Tetrahedron Letters, vol. 50, No. 23, Jun. 10, 2009, pp. 2758-2761.
International Search Report and Written Opinion in related PCT/US2015/038596 dated Sep. 30, 2015, 22 pages.
International Preliminary Report on Patentability in related PCT/US2015/038596 dated Jan. 12, 2017, 13 pages.
Miyaura, N. et al., "Palladium-Catalyzed Cross-Coupling Reactions of Organo Carbon Compounds," Chem Rev. 1995, 95, 2457-2483.
Kotha, et al., "Recent Applications of the Suzuki-Miyaura Cross-Coupling Reaction in Organic Synthesis," Tetrahedron, (2002), 58, 9633-9695.
Long, et al., "The Comorbidities of Diabetes and Hypertension: Mechanisms and Approach to Target Organ Protection," J Clin Hypertens, Apr. 2011; 13(4), 244-251.
Cleland, "Cardiovascular Risk in Double Diabetes Mellitus—When Two Worlds Collide," Nature Review, Endocrinology 8, 476-485.
Zinman, "Initial Combination Therapy for Type 2 Diabetes Mellitus: Is it ready for prime time?" The American Journal of Medicine 124, S19-34.
Muccio, et al., "Conformationally Defined Retinoic Acid Analogues," 4. Potential New Agents for Acute Promyelocytic and Juvenile Myelomonocytic Leukemias, Journal of Medicinal Chemistry 41, 1679-1687.
Atigadda, et al., Conformationally Defined Retinoic Acid Analagies. 5. Large-scale synthesis and mammary cancer chemopreventive activity for (2E,4E,6Z,8E)-8-(3',4'-dihydro-1'(2'H)-napthalen-1'-ylidene)-3,7-dimethyl-2,4,6-octatrienoic acid (9cUAB30), Journal of Medicinal Chemistry 46, 3766-3769.
Boerma, et al., "Defining the Communication Between Agonist and Coactivator Binding in the Retinoid X Receptor α Ligand Binding Domain," The Journal of Biological Chemistry, vol. 289, No. 2, pp. 814-823, Jan. 10, 2014.
Desphande, et al., "Methyl-substituted Conformationally Constrained Rexinoid Agonists for the Retinoid X Receptors Demonstrate Improved Efficacy for Cancer Therapy and Prevention," Bioorg Med Chem, Jan. 1, 2014, 22(6), 178-185.
Kolesar, et al., "A Pilot, First-in-Human, Pharmacokinetic Study of 9cUAB30 in Healthy Volunteers," Cancer Prev Res, Dec. 3, 2010(12); 1565-1570 2010.
Vedell, et al., "Effects on Gene Expression in Rat Liver After Administration of RXR Agonists: UAB30, 4-methyl-UAB30, and Targretin (Bexarotene)," Molecular Pharmacology 83, 698-708.
Vedell, et al., "Global Molecular Changes in Rat Livers Treated with RXR Agonists: A Comparison Using Transciptomics and Proteomics," Pharmacology Research & Perspectives 2(6), 2014, e00074.
Freedman, Obesity-United States, 1988-2008. MMWR Surveill Summ 60 Suppl. 73-77.
Tang, et al., PPARgamma Agonists: Safety Issues in Heart Failure, Diabetes, Obesity & Metabolism 9, 447-454.

Tirona, et al., "Nuclear Receptors and Drug Disposition Gene Regulation," Journal of Pharmaceutical Sciences 94, 1169-1186.
Han, et al., "Beneficial Vascular and Metabolic Effects of Peroxisome Proliferator-Activated Receptor-α Activators," Hypertension 46, 1086-1092.
Ijpenberg, et al., "In Vivo Activation of PPAR Target Genes by RXR Homodimers," The EMBO Journal (2004) 23, 2083-2091.
Perez, et al., "Modulation of RXR Function Through Ligand Design," Biochimica et Biophysica Acta 1821, 57-69.
Pinaire, et al., "Therapeutic Potential of Retinoid X Receptor Modulators for the Treatment of the Metabolic Syndrome," PPAR Research, vol. 2007, Article ID 94156, 12 pages.
Huang, et al., "Retinoic Acid Actions Through Mammalian Nuclear Receptors," Chem Rev 2-14 Jan. 8; 114(1); 233-254.
Ohsawa, F. et al., "Mechanism of Retinoid X Receptor Partial Agonistic Action of 1-(3,5,5,8,8-Pentamethyl-5,6,7,8-tetrahydro-2-naphthyl)-1H-benzotriazole-5-carboxylic Acid and Structural Development to Increase Potency," J. Med. Chem. 56, 1865-1877 (2013).
Lalloyer, F. et al., "Rexinoid Bexarotene Modulates Triglyceride but not Cholesterol Metabolism via Gene-Specific Permissivity of the RXR/LXR Heterodimer in the Liver," Arterioscler Thromb Vasc Biol 2009;29:1488-1495.
Tsai, J. Y. et al., "Influence of Dark Phase Restricted High Fat Feeding on Myocardial Adaptation in Mice," J Mol Cell Cardiol. Feb. 2013; 55: 147-155.
Janssen, J. S. et al., "A Rexinoid Antagonist Increases the Hypothalamic-Pituitary-Thyroid Set Point in Mice and Thyrotrope Cells," Mol Cell Endocrinol Jun. 6, 2011; 339(1-2): 1-6.
Klopper, J. P. et al., "In Vivo and Microarray Analysis of Rexinoid-Responsive Anaplastic Thyroid Carcinoma," Clin Cancer Res 2008:14(2) Jan. 15, 2008 589-596.
Golden, W. M. et al., "Single-Dose Rexinoid Rapidly and Specifically Suppresses Serum Thyrotropin in Normal Subjects," The Journal of Clinical Endocrinology & Metabolism 92(1), 124-130, doi:10.1210/jc.2006-0696 (2007).
Sharma, V. et al., "Effects of Rexinoids on Thyrotrope Function and the Hypothalamic-Pituitary-Thyroid Axis," Endocrinology 147(3): 1438-1451.
Liu, S. et al., "Mechanism of Selective Retinoid X Receptor Agonist-Induced Hypothyroidism in the Rat," Endocrinology 143(8), 2880-2885 (2002).
Xu, H. et al. "Chronic Inflammation in Fat Plays a Crucial Role in the Development of Obesity-Related Insulin Resistance," The Journal of Clinical Investigation; vol. 112(12), Dec. 2003, 1821-1830.
Weisberg, S. P. et al., "Obesity is Associated with Macrophage Accumulation in Adipose Tissue," The Journal of Clinical Investigation, vol. 112(12), Dec. 2003, 1796-1808.
Bligh, E. G. & Dyer, W. J., "A Rapid Method of Total Lipid Extraction and Purification," Can. J. Biochem. and Physiol. vol. 37(8), Aug. 1959, 911-917.
Wang, P. et al., "Peroxisome Proliferator-Activated Receptor σ Is an Essential Transcriptional Regulator for Mitochondrial Protection and Biogenesis in Adult Heart," Circulation Research 106, 911-919, 2010.
Xia, G. et al., "Structure, Energetics, and Dynamics of Binding Coactivator Peptide to the Human Retinoid X Receptor Alpha Ligand Binding Domain Complex with 9-cis-Retinoic Acid," Biochemistry, Jan. 11, 2011; 50(1), 93-105.
Communication Pursuant to Article 94(3) EPC issued in European Patent Application No. 15815081.3 on dated Mar. 7, 2019.
Application No. MX/a/2017/000087, Office Action, dated Aug. 6, 2020, 6 pages with English translation.

* cited by examiner

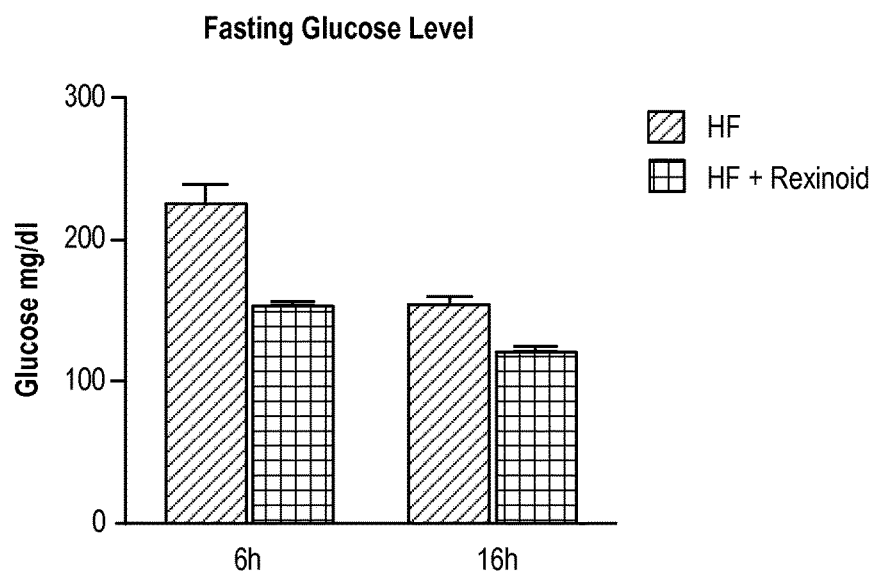
FIG. 5
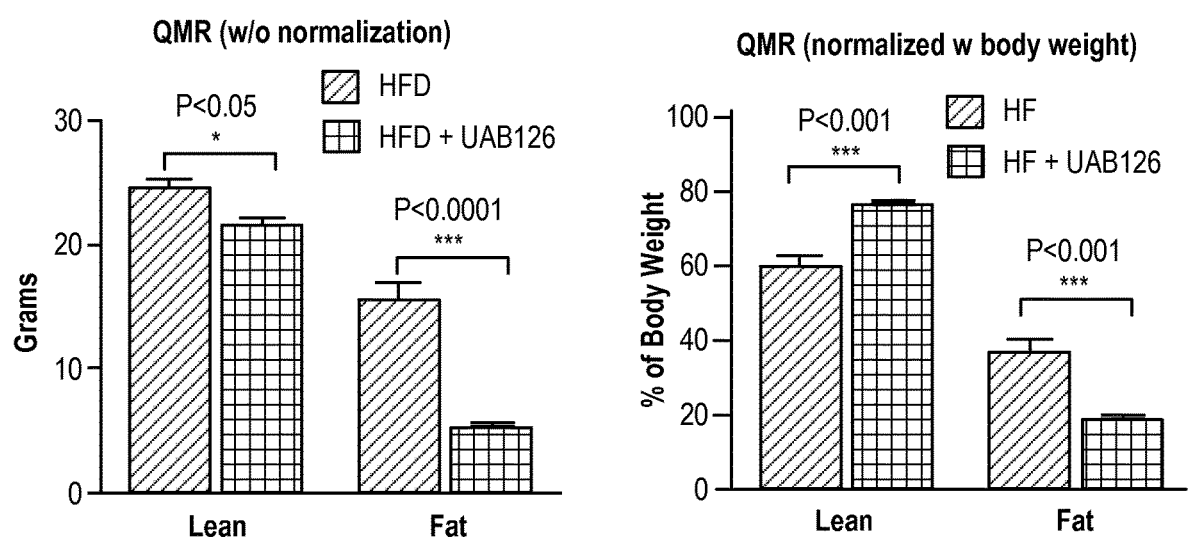
FIG. 6A
FIG. 6B

REXINOID COMPOUNDS AND METHODS OF USING REXINOID COMPOUNDS FOR TREATING METABOLIC DISORDERS AND CANCER

CROSS-REFERENCE TO PRIORITY APPLICATION

This application claims priority to U.S. Provisional Application No. 62/019,170, filed on Jun. 30, 2014, which is incorporated herein by reference in its entirety.

BACKGROUND

The underlying causes of cardiometabolic disorders include imbalances in metabolic and inflammatory processes. The nuclear receptor family of transcription factors is involved in both energy homeostasis and inflammation, leading to the concept that an effective strategy for cardiometabolic disease treatment may include pharmacologically targeting one or more nuclear receptors. To date, this strategy has lead only to partial success. For example, PPARγ agonists (thiazolidinediones, TZD) have insulin sensitizing effects but can also cause water retention and heart failure. The PPARγ agonists have lipid lowering effects but can cause gallstone and hepatotoxicity. It is clear that a novel class of nuclear receptor agonists/antagonists with an optimal therapeutic index would be beneficial for the treatment of cardiometabolic diseases. The retinoid X nuclear receptors (RXRs) form heterodimers with many nuclear receptors, whose signaling maintains metabolic homeostasis. As such they are potential drug targets for treating metabolic syndrome. Several rexinoids (specific RXR agonist) have been tested for glucose-lowering, insulin-sensitizing, and anti-obesity effects. Even though these studies have shown that rexinoids have beneficial effects on glucose metabolism, most of these rexinoids have dose-limiting side effects including elevation of serum triglyceride levels and hepatomegaly and an alteration of the thyroid hormone axis. These side effects may be due to the potent and non-selective stimulation of RXR signaling.

SUMMARY

Rexinoid compounds and methods for the treatment of metabolic disorders and cancer are provided. A class of rexinoid compounds includes compounds of the following formula:

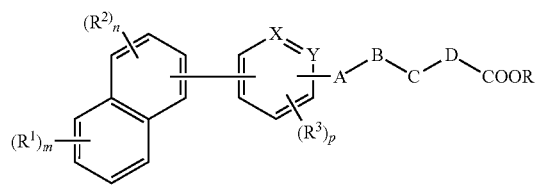

and pharmaceutically acceptable salts or prodrugs thereof. In these compounds, m is 0-4, n is 0-3, and p is 0-2; R is selected from the group consisting of H, alkyl, benzyl, aryl, or heteroaryl; each $R^1$, $R^2$, and $R^3$ are independently selected from the group consisting of H, halo, $C_1$-$C_6$ alkyl, $C_1$-$C_6$ haloalkyl, $C_2$-$C_6$ alkenyl, $C_2$-$C_6$ alkynyl, aryl, $OR^4$, $NH_2$, $NHR^4$, $NR^4R^5$, and $SR^4$, where $R^4$ and $R^5$ are each independently selected from H, $C_1$-$C_6$ alkyl, and —C(O)$R^6$, where $R^6$ is H, $C_1$-$C_6$ alkyl, or aryl; X and Y are each independently selected from the group consisting of C—H, C—($C_1$-$C_6$ alkyl), N, O, and S, wherein when X is O or S, then Y is absent such that a five-membered heteroaromatic ring is formed or when Y is O or S, then X is absent such that a five-membered heteroaromatic ring is formed; and A, B, C and D are each independently selected from the group consisting of —$CH_2$—, —CHF—, —$CF_2$—, —CHCl—, —$CCl_2$—, —CHBr—, —$CBr_2$—, —CH($C_1$-$C_6$ alkyl)-, —C($C_1$-$C_6$ alkyl)$_2$-, —CH ($C_1$-$C_6$ haloalkyl)-, —C($C_1$-$C_6$ haloalkyl)$_2$-, —CH═CH—, —C($R_5$)═CH—, —CH═C($R_5$)—, —C($R_5$)═CR—, and —C≡C—, or one or more of A, B, C, or D is absent such that the remaining units connect to form a chain.

Optionally, the compound has a formula selected from the group consisting of:

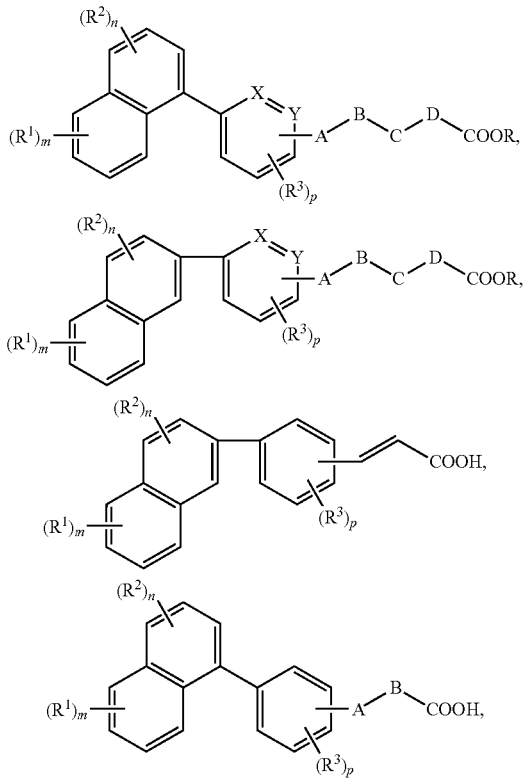

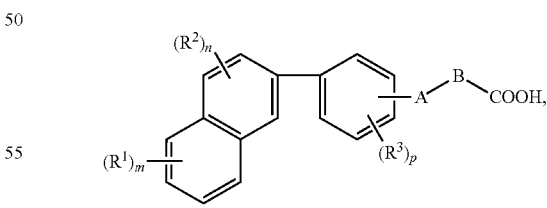

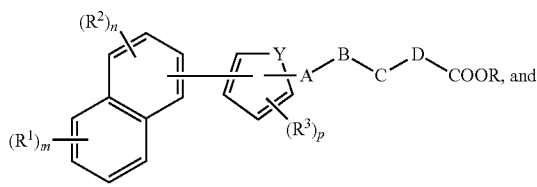

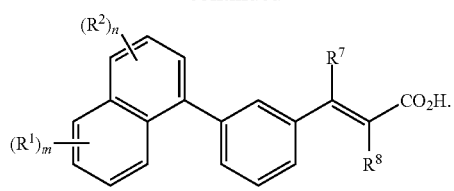
Optionally, the compound is selected from the group consisting of:
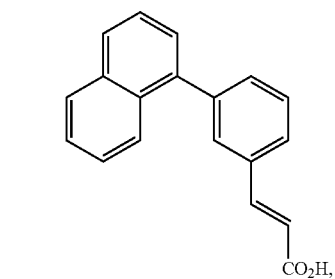
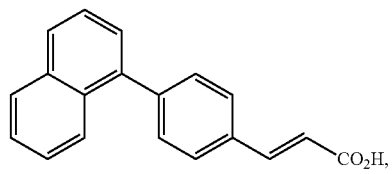
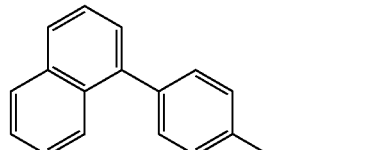
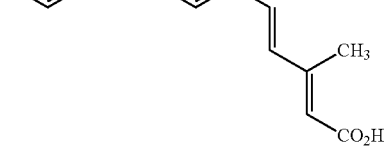
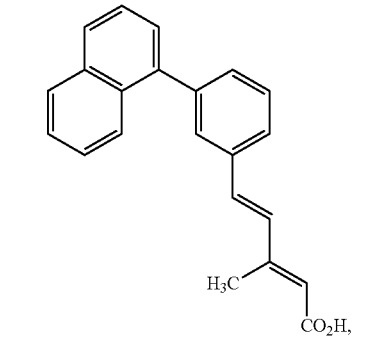
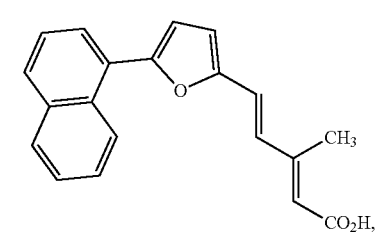
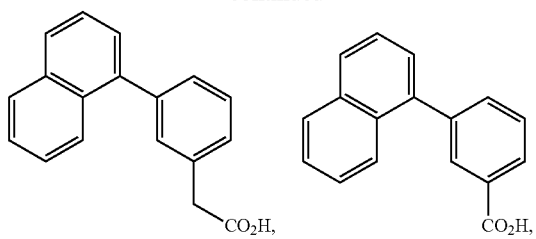
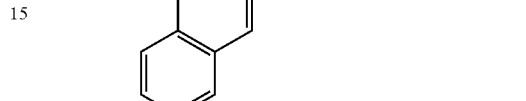
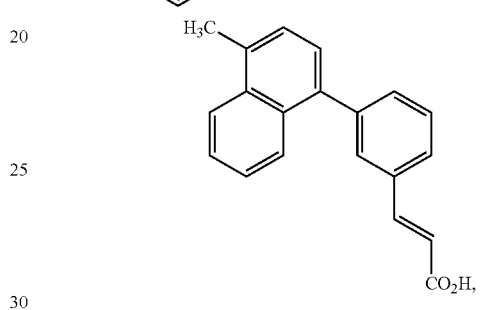
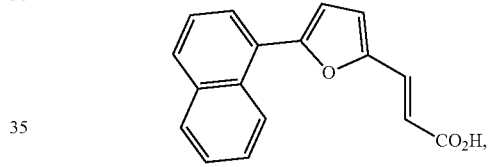
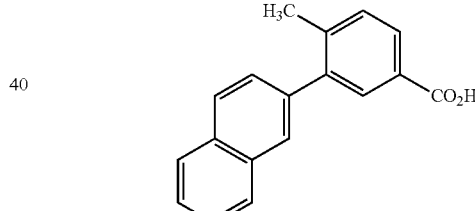
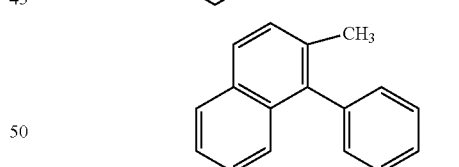
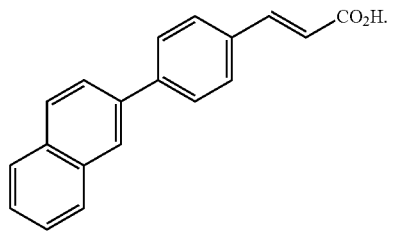

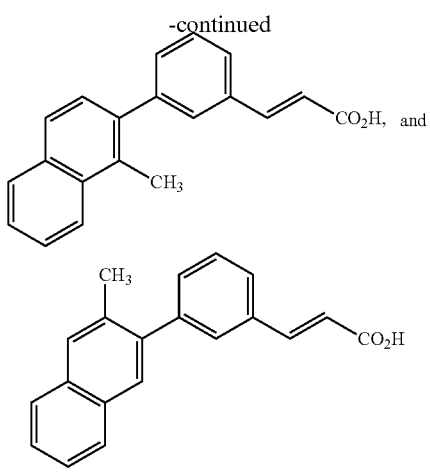

A class of rexinoid compounds includes compounds of the following formula:

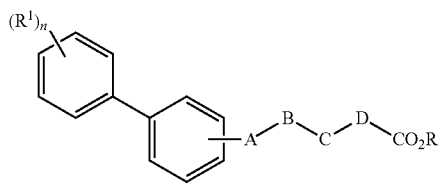

and pharmaceutically acceptable salts or prodrugs thereof. In these compounds, n is 0-5; R is selected from the group consisting of H, alkyl, benzyl, aryl or heteroaryl; each $R^1$ is independently selected from the group consisting of H, halo, $C_1$-$C_6$ alkyl, $C_1$-$C_6$ haloalkyl, $C_2$-$C_6$ alkenyl, $C_2$-$C_6$ alkynyl, aryl, $OR^4$, $NH_2$, $NHR^4$, $NR^4R^5$, and $SR^4$, where $R^4$ and $R^5$ are each independently selected from H, $C_1$-$C_6$ alkyl, and —C(O)$R^6$, where $R^6$ is H, $C_1$-$C_6$ alkyl, or aryl; and A, B, C and D are each independently selected from the group consisting of —CH$_2$—, —CHF—, —CF$_2$—, —CHCl—, —CCl$_2$—, —CHBr—, —CBr$_2$—, —CH($C_1$-$C_6$ alkyl)-, —C($C_1$-$C_6$ alkyl)$_2$-, —CH ($C_1$-$C_6$ haloalkyl)-, —C($C_1$-$C_6$ haloalkyl)$_2$-, —CH=CH—, —C($R^3$)=CH—, —CH=C($R^3$)—, —C($R^3$)=CR—, and —C≡C—, or one or more of A, B, C, or D is absent such that the remaining units connect to form a chain.

Optionally, the compound has a formula selected from the group consisting of:

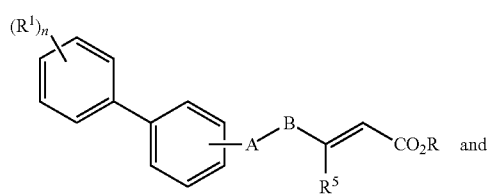

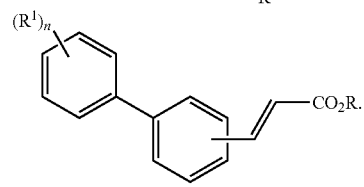

Optionally, the compound is selected from the group consisting of:

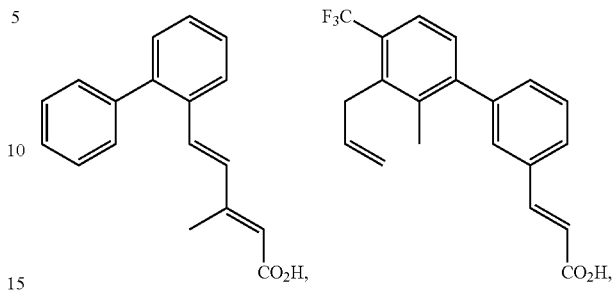

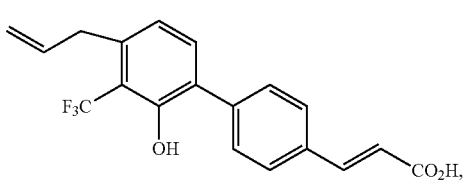

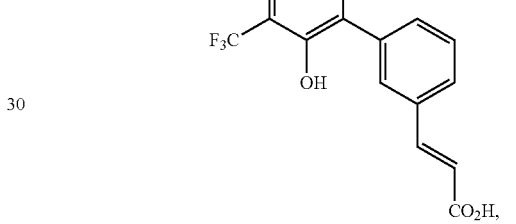

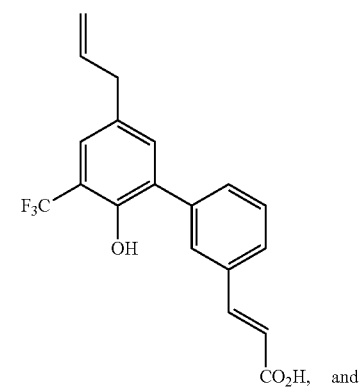

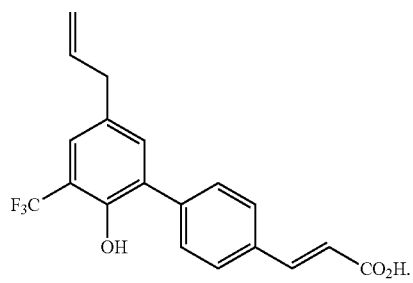

A class of rexinoid compounds includes compounds of the following formula:

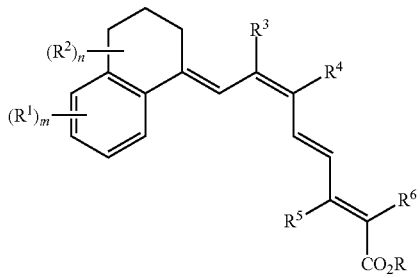

or pharmaceutically acceptable salts or prodrugs thereof. In these compounds, each $R^1$, each $R^2$, $R^3$, $R^4$, $R^5$, and $R^6$ are each independently selected from the group consisting of hydrogen, fluoro, $C_1$-$C_6$ alkyl, and fluoro-substituted $C_1$-$C_6$ alkyl, wherein at least one of $R^3$, $R^4$, $R^5$, and $R^6$ is fluoro or a fluoro-substituted $C_1$-$C_6$ alkyl. Optionally, $R^3$ and $R^5$ are not simultaneously methyl.

Optionally, the compound is selected from the group consisting of:

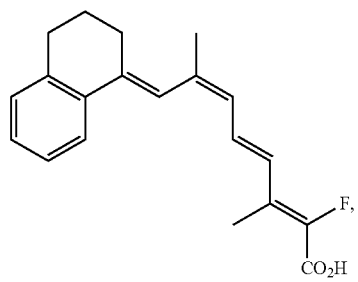

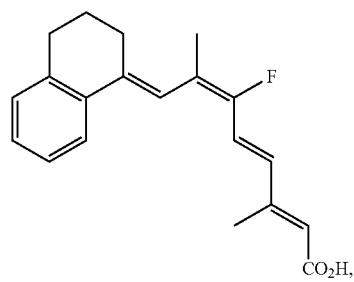

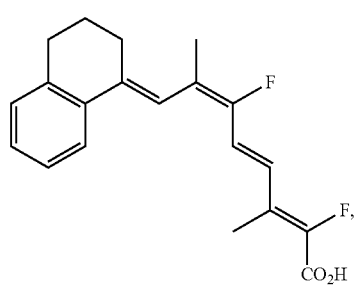

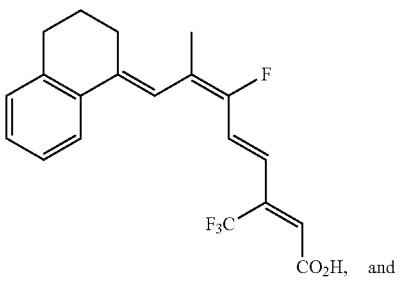

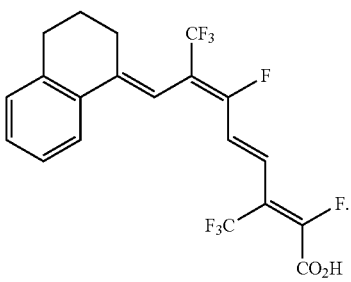

Also provided herein are pharmaceutical compositions comprising one or more of the compounds described above and a pharmaceutically acceptable carrier.

Further provided herein are methods of treating or preventing a metabolic disorder in a subject. A method of treating or preventing a metabolic disorder in a subject includes administering to a subject an effective amount of a compound as described herein. Optionally, administering the compound provides a glucose-lowering effect, an insulin-sensitizing effect, and/or a plasma triglyceride lowering effect.

Also provided herein are methods of treating or preventing insulin resistance, glucose intolerance, obesity, steatosis or inflammation in a subject comprising administrating to a subject in thereof an effective amount of a compound as described herein. Optionally, the subject is a mammalian subject (including, e.g., a dog, a cat, a rodent, or a human). Optionally, the subject is obese or morbidly obese. Optionally, the subject is pre-diabetic or diabetic. The compound can be administered orally, topically, intranasally, intravenously, subcutaneously, intradermally, transdermally intramucosally intramuscularly, by inhalation spray, rectally, nasally, sublingually, buccally, vaginally or via an implanted reservoir. Optionally, the compound is

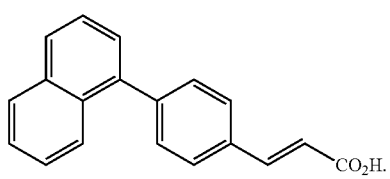

Further provided herein are methods of treating or preventing cancer in a subject. A method of treating or preventing cancer in a subject includes administering to a subject an effective amount of a compound as described herein. Optionally, the cancer is epithelial cancer, such as skin cancer or breast cancer. Optionally, the compound is

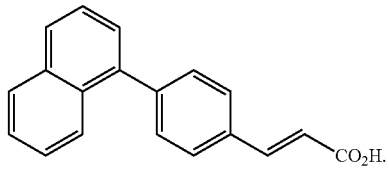 [SMILES: O=C(O)/C=C/c1ccc(-c2cccc3ccccc23)cc1]

Also provided herein are kits for treating or preventing a metabolic disorder, insulin resistance, glucose intolerance, obesity, steatosis, inflammation, or cancer. A kit for treating a metabolic disorder, insulin resistance, glucose intolerance, obesity, steatosis or inflammation as described herein comprises a compound or composition as described herein and a container or delivery device, optionally including the compound. A kit for treating or preventing cancer comprises a compound or composition as described herein and a container or delivery device, optionally including the compound. Optionally, the kits described herein further comprise instructions regarding use of the kit and/or contents thereof.

DESCRIPTION OF DRAWINGS

FIG. 5 is a graph showing the fasting glucose levels of mice over time on a high fat diet without treatment (HF) and with treatment using Compound UAB126 (HF+Rexinoid).

FIG. 6A is a graph showing the percent body weight of lean body mass and fat mass for mice on a high fat diet without treatment (HF) and with treatment using Compound UAB126 (HF+UAB126) without normalization.

FIG. 6B is a graph showing the percent body weight of lean body mass and fat mass for mice on a high fat diet without treatment (HF) and with treatment using Compound UAB126 (HF+UAB126), normalized with body weight.

Figure 1:
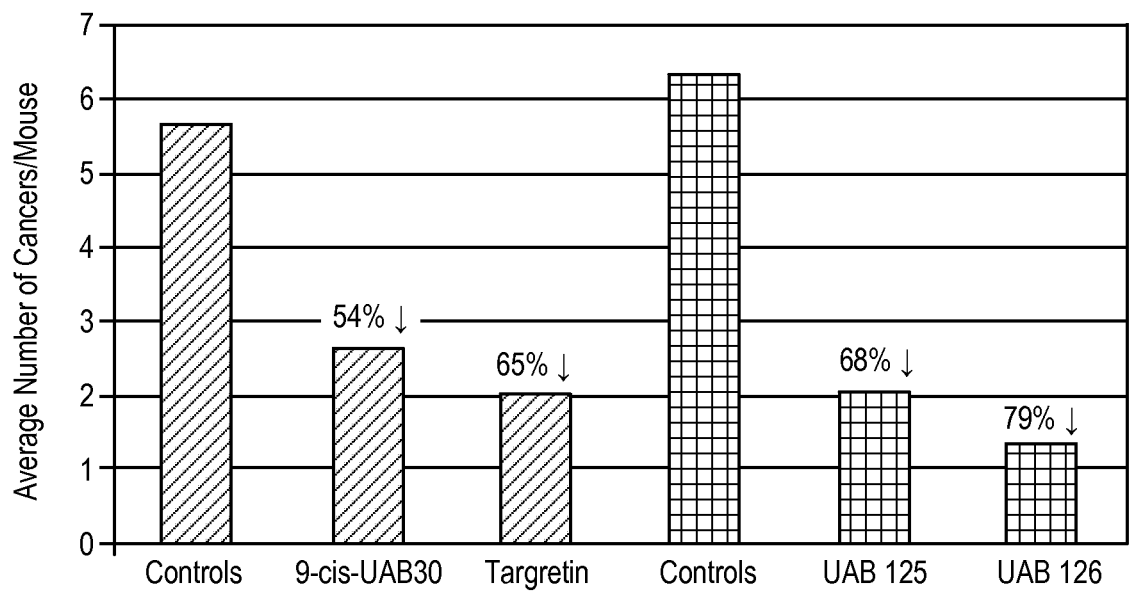
FIG. 1 is a graph showing the efficacy of 9-cis-UAB30, TARGRETIN, Compound UAB125, and Compound UAB126 in preventing the formation of mammary cancers in ErbB2$^{+/-}$ female mice. The first bar represents the controls for 9-cis-UAB30 and TARGRETIN. The fourth bar represents the controls for UAB125 and UAB126.

The details of one or more embodiments are set forth in the description below. Other features, objects, and advantages will be apparent from the description and from the claims.

DETAILED DESCRIPTION

The compounds described herein present classes of rexinoids for treating and preventing metabolic disorders and/or cancer.

I. Compounds

A class of rexinoids described herein is represented by Formula I:

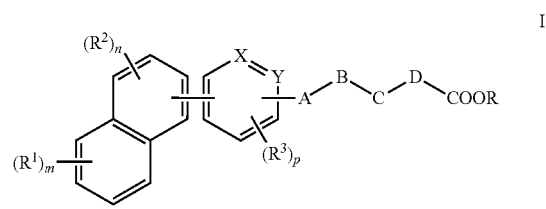

and pharmaceutically acceptable salts or prodrugs thereof.

In Formula I, m is 0-4 (i.e., 0, 1, 2, 3, or 4); n is 0-3 (i.e., 0, 1, 2, or 3); and p is 0-2 (i.e., 0, 1, or 2).

Also, in Formula I, R is selected from the group consisting of H, alkyl, benzyl, aryl or heteroaryl.

Additionally, in Formula I, each $R^1$, $R^2$, and $R^3$ are independently selected from the group consisting of H, halo, $C_1$-$C_6$ alkyl, $C_1$-$C_6$ haloalkyl, $C_2$-$C_6$ alkenyl, $C_2$-$C_6$ alkynyl, aryl, hydroxyl, alkoxyl, aryloxyl, amino, thio, and carboxyl. Optionally, $R^1$, $R^2$, and $R^3$ are each independently selected from methyl, ethyl, propyl, isopropyl, butyl, t-butyl, fluoro, bromo, chloro, $CF_3$, $CF_2CF_3$, $CH_2CF_3$, $OR^4$, $NH_2$, $NHR^4$, $NR^4R^5$, and $SR^4$, where $R^4$ and $R^5$ are each independently selected from H, $C_1$-$C_6$ alkyl, and —C(O)$R^6$, where $R^6$ is H, $C_1$-$C_6$ alkyl, or aryl.

Also, in Formula I, X and Y are each independently selected from the group consisting of C—H, C—($C_1$-$C_6$ alkyl), N, O, and S, wherein when X is O or S, then Y is absent such that a five-membered heteroaromatic ring is formed and when Y is O or S, then X is absent such that a five-membered heteroaromatic ring is formed.

Further, in Formula I, A, B, C and D are each independently selected from the group consisting of —CH$_2$—, —CHF—, —CF$_2$—, —CHCl—, —CCl$_2$—, —CHBr—, —CBr$_2$—, —CH($C_1$-$C_6$ alkyl)-, —C($C_1$-$C_6$ alkyl)$_2$-, —CH($C_1$-$C_6$ haloalkyl)-, —C($C_1$-$C_6$ haloalkyl)$_2$-, —CH═CH—, —C($R_5$)═CH—, —CH═C($R_5$)—, —C($R_5$)═CR—, and —C≡C—, or one or more of A, B, C, or D is absent such that the remaining units connect to form a chain. Adjacent units, such as A and B or C and D, when taken together, can form an alkenyl unit: —C($R_7$)═C($R_8$)—, where $R^7$ and $R^8$ are each independently selected from the group consisting of H, halo, $C_1$-$C_6$ alkyl, $C_1$-$C_6$ haloalkyl, $C_2$-$C_6$ alkenyl, $C_2$-$C_6$ alkynyl, aryl, hydroxyl, alkoxyl, aryloxyl, amino, thio, and carboxyl.

Formula I includes Structure I-A:

Structure I-A

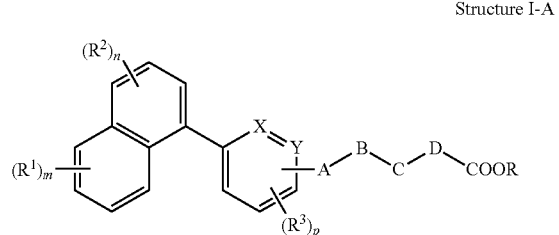

In Structure I-A, m, n, p, R, R¹, R², R³, X, Y, A, B, C, and D are as defined above for Formula I.

Formula I also includes Structure I-B:

Structure I-B

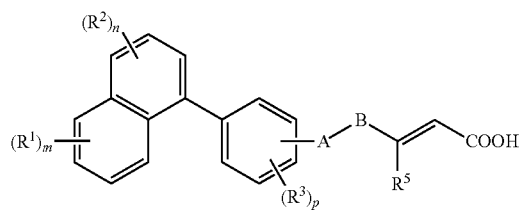

Formula I also includes Structure I-C:

Structure I-C

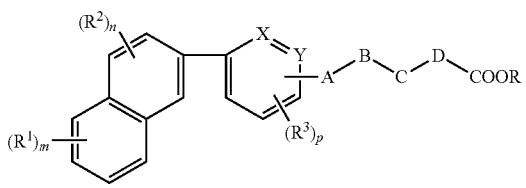

In Structure I-C, m, n, p, R, R¹, R², R³, X, Y, A, B, C, and D are as defined above for Formula I.

Formula I also includes Structure I-D:

Structure I-D

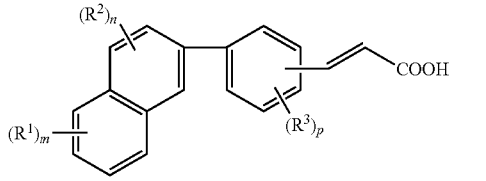

In Structure I-D, m, n, p, R¹, R², and R³ are as defined above for Formula I.

Formula I also includes Structure I-E:

Structure I-E

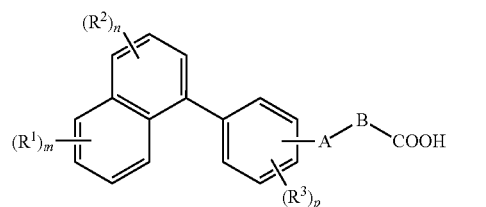

In Structure I-E, m, n, p, R¹, R², R³, A, and B are as defined above for Formula I.

Formula I also includes Structure I-F:

Structure I-F

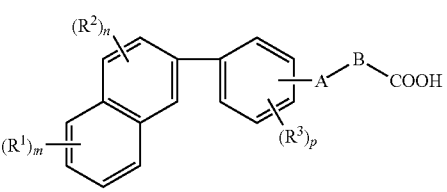

In Structure I-F, m, n, p, R¹, R², R³, A, and B are as defined above for Formula I.

Formula I also includes Structure I-G:

Structure I-G

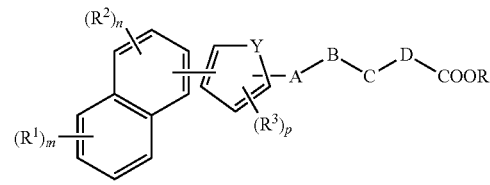

In Structure I-G, m, n, p, R, R¹, R², R³, Y, A, B, C, and D are as defined above for Formula I.

Formula I also includes Structure I-H:

Structure I-H

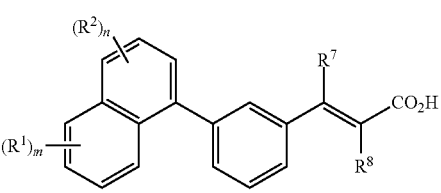

In Structure I-H, m, n, R¹, R², R⁷, and R⁸ are as defined above for Formula I.

Examples of Formula I include the following compounds:

Compound 1 (UAB122)

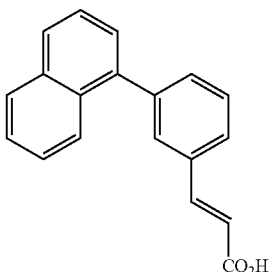

Compound 2 (UAB126)

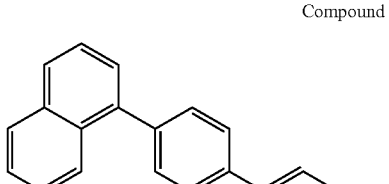

Compound 3 (UAB118)
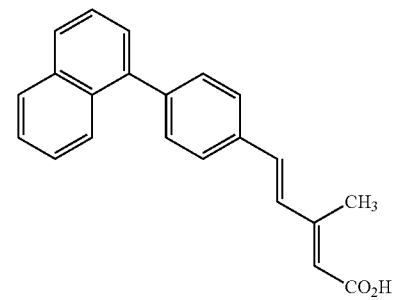
Compound 4 (UAB119)
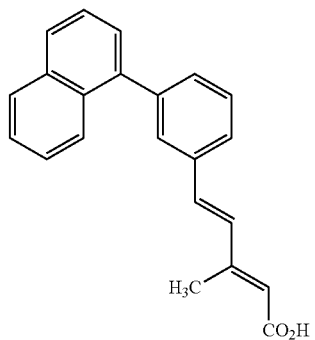
Compound 5 (UAB120)
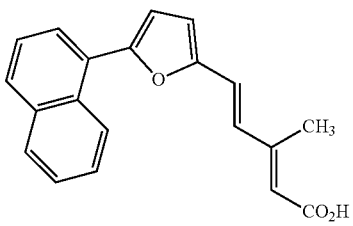
Compound 6 (UAB121)
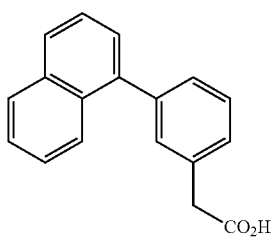
Compound 7
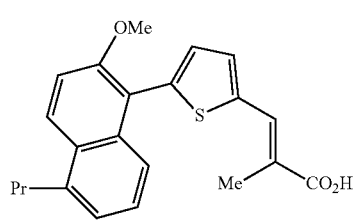
Compound 8 (UAB123)
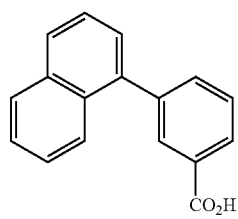
Compound 9 (UAB124)
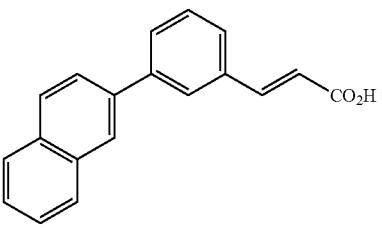
Compound 10 (UAB125)
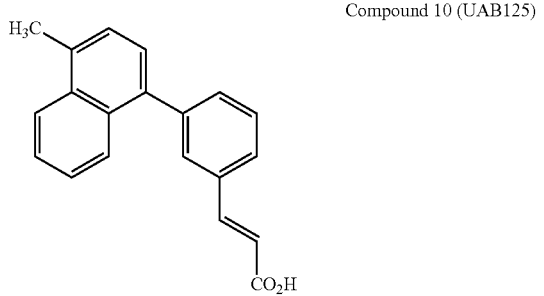
Compound 11 (UAB127)
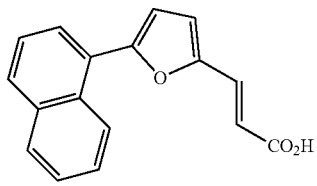
Compound 12 (UAB128)
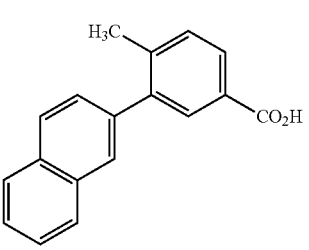
Compound 13 (UAB129)
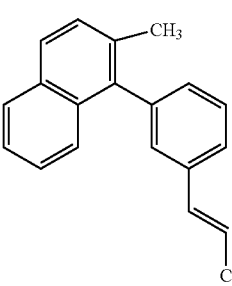
Compound 14 (UAB130)
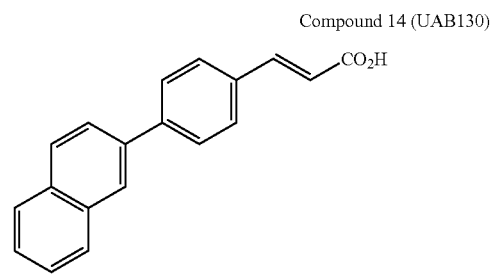

-continued

Compound 15 (UAB131)

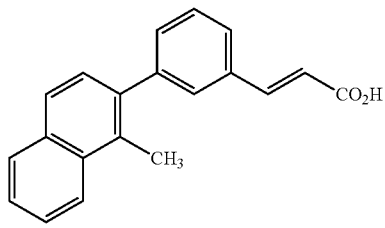

Compound 16 (UAB132)

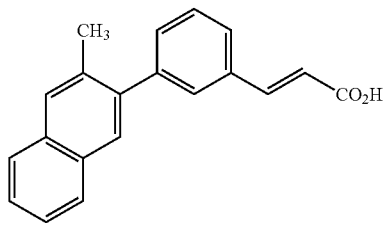

Compound 17

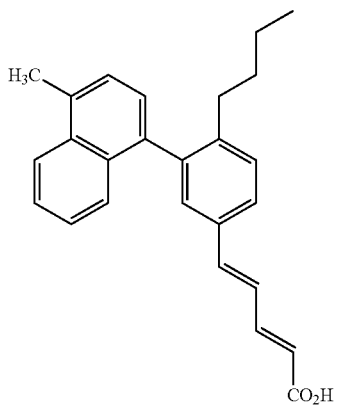

Compound 18

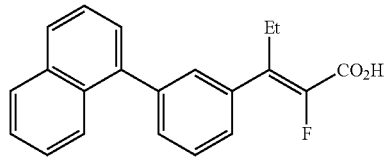

Compound 19

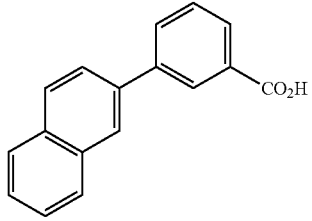

Compound 20

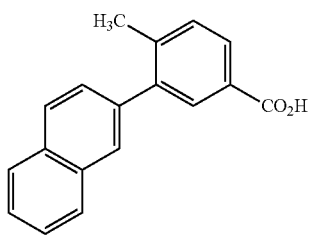

A class of rexinoids described herein is represented by Formula II:

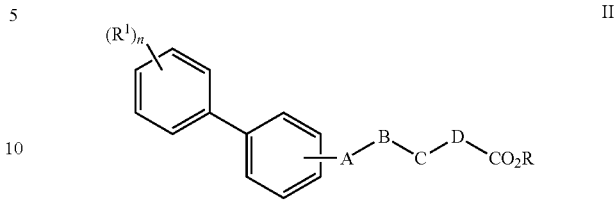

and pharmaceutically acceptable salts or prodrugs thereof.

In Formula II, n is 0-5 (i.e., 0, 1, 2, 3, 4, or 5).

Also, in Formula II, R is selected from the group consisting of H, alkyl, benzyl, aryl or heteroaryl.

Additionally, in Formula II, each $R^1$ is independently selected from the group consisting of H, halo, $C_1$-$C_6$ alkyl, $C_1$-$C_6$ haloalkyl, $C_2$-$C_6$ alkenyl, $C_2$-$C_6$ alkynyl, aryl, hydroxyl, alkoxyl, aryloxyl, amino, thio, and carboxyl. Optionally, $R^1$ is selected from methyl, ethyl, propyl, isopropyl, butyl, t-butyl, fluoro, bromo, chloro, $CF_3$, $CF_2CF_3$, $CH_2CF_3$, $OR^2$, $NH_2$, $NHR^2$, $NR^2R^3$, and $SR^2$, where $R^2$ and $R^3$ are each independently selected from H, $C_1$-$C_6$ alkyl, and —C(O)$R^4$, where $R^4$ is H, $C_1$-$C_6$ alkyl, or aryl.

Further, in Formula II, A, B, C and D are each independently selected from the group consisting of —$CH_2$—, —CHF—, —$CF_2$—, —CHCl—, —$CCl_2$—, —CHBr—, —$CBr_2$—, —CH($C_1$-$C_6$ alkyl)-, —C($C_1$-$C_6$ alkyl)$_2$-, —CH($C_1$-$C_6$ haloalkyl)-, —C($C_1$-$C_6$ haloalkyl)$_2$-, —CH=CH—, —C($R^3$)=CH—, —CH=C($R^3$)—, —C($R^3$)=CR—, and —C≡C—, or one or more of A, B, C, or D is absent such that the remaining units connect to form a chain. Adjacent units, such as A and B or C and D, when taken together, can form an alkenyl unit: —C($R^5$)=C($R^6$)—, where $R^5$ and $R^6$ are each independently selected from the group consisting of H, halo, $C_1$-$C_6$ alkyl, $C_1$-$C_6$ haloalkyl, $C_2$-$C_6$ alkenyl, $C_2$-$C_6$ alkynyl, aryl, hydroxyl, alkoxyl, aryloxyl, amino, thio, and carboxyl.

Formula II includes Structure II-A:

Structure II-A

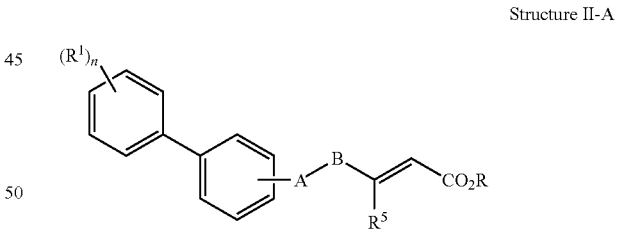

In Structure II-A, n, R, $R^1$, $R^5$, A, and B are as defined above for Formula II.

Formula II also includes Structure II-B:

Structure II-B

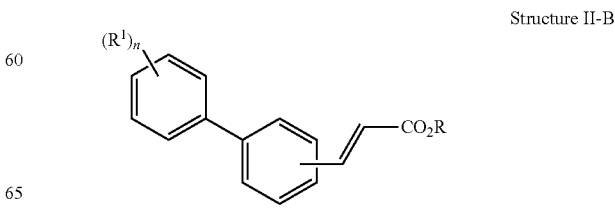

In Structure II-B, n, R, and $R^1$ are as defined above for Formula II.

Examples of Formula II include the following compounds:

Compound 22 (UAB140)

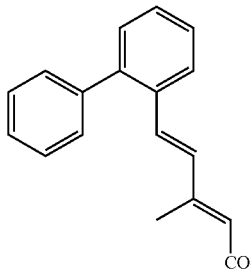

Compound 23

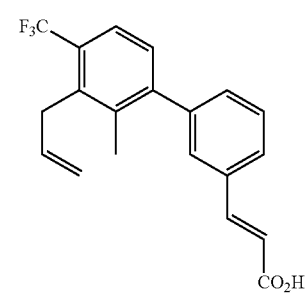

Compound 24

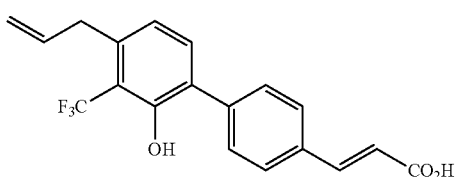

Compound 25

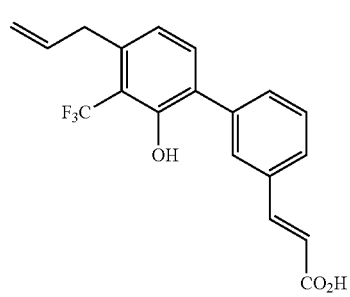

Compound 26

Compound 27

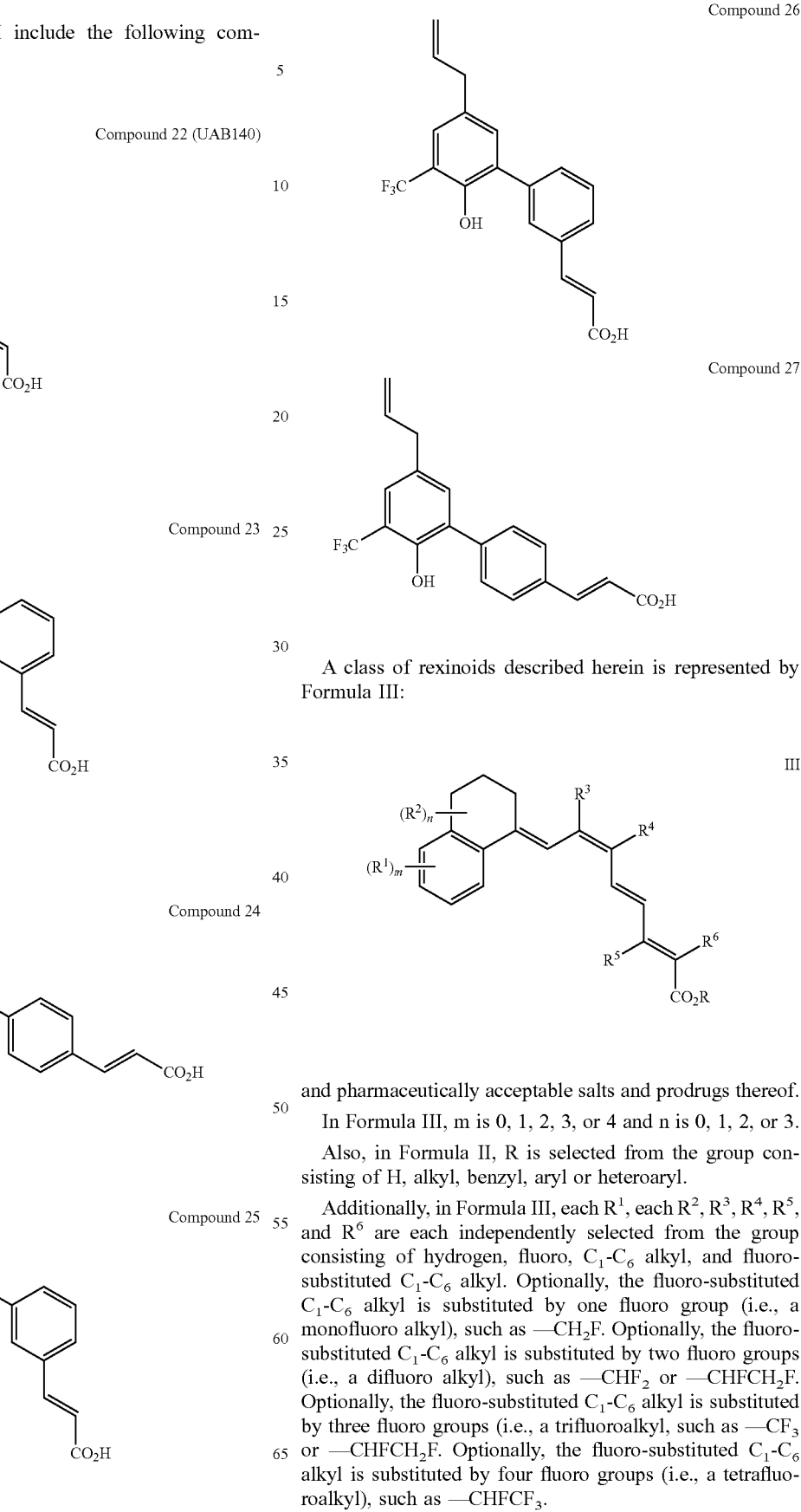

A class of rexinoids described herein is represented by Formula III:

III and pharmaceutically acceptable salts and prodrugs thereof.

In Formula III, m is 0, 1, 2, 3, or 4 and n is 0, 1, 2, or 3.

Also, in Formula II, R is selected from the group consisting of H, alkyl, benzyl, aryl or heteroaryl.

Additionally, in Formula III, each $R^1$, each $R^2$, $R^3$, $R^4$, $R^5$, and $R^6$ are each independently selected from the group consisting of hydrogen, fluoro, $C_1$-$C_6$ alkyl, and fluoro-substituted $C_1$-$C_6$ alkyl. Optionally, the fluoro-substituted $C_1$-$C_6$ alkyl is substituted by one fluoro group (i.e., a monofluoro alkyl), such as —$CH_2F$. Optionally, the fluoro-substituted $C_1$-$C_6$ alkyl is substituted by two fluoro groups (i.e., a difluoro alkyl), such as —$CHF_2$ or —$CHFCH_2F$. Optionally, the fluoro-substituted $C_1$-$C_6$ alkyl is substituted by three fluoro groups (i.e., a trifluoroalkyl, such as —$CF_3$ or —$CHFCH_2F$. Optionally, the fluoro-substituted $C_1$-$C_6$ alkyl is substituted by four fluoro groups (i.e., a tetrafluoroalkyl), such as —$CHFCF_3$.

In Formula III, at least one of $R^3$, $R^4$, $R^5$, and $R^6$ is fluoro or a fluoro-substituted $C_1$-$C_6$ alkyl. Optionally, at least one of $R^3$, $R^4$, $R^5$, and $R^6$ is fluoro, monofluoromethyl, difluoromethyl, or trifluoromethyl.

Optionally, $R^3$ and $R^5$ are not simultaneously methyl.

Examples of Formula III include the following compounds:

Compound 28 (14-F-9cis-UAB30)

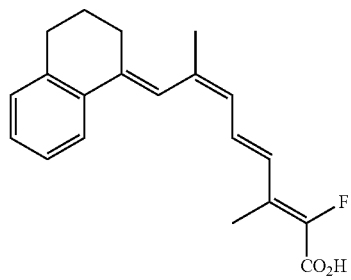

Compound 29 (10-F-9cis-UAB30)

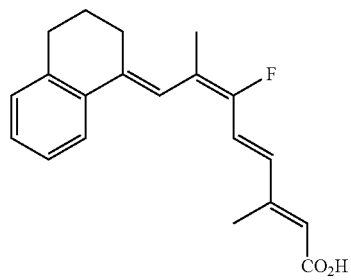

Compound 30 (10,14-diF-9cis-UAB30)

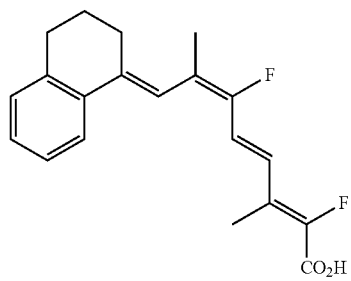

Compound 31

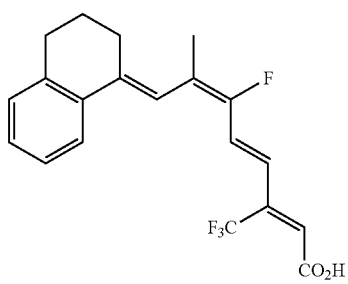

Compound 32

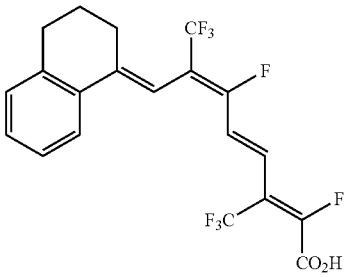

The compound described herein is not the following:

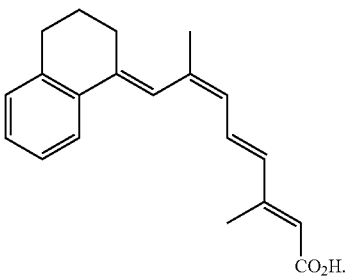 [SMILES: CC(=C/C=C/C(C)=C/C(=O)O)/C=C1\CCCc2ccccc21]

The term about, as used herein when referring to a measurable value, such as, for example, an amount or concentration, is meant to encompass variations of ±20%, ±10%, ±5%, ±1%, ±0.5%, or even ±0.1% of the specified amount. A range provided herein for a measurable value may include any other range and/or individual value therein.

Alkyl, as used herein, refers to a straight or branched chain hydrocarbon containing from 1 or 2 to 10 or 20 or more carbon atoms (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, etc.). Optionally, the alkyl can be a lower alkyl. "Lower alkyl" refers to straight or branched chain alkyl having from 1 to 3, or from 1 to 5, or from 1 to 8 carbon atoms. Representative examples of alkyls include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. Alkyl groups as described herein are optionally substituted (e.g., from 1 to 3 or 4 times) with substituents independently selected from, but not limited to, H, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocyclo, heteroaryl, hydroxy, nitro, oxo, oxy, peptide, sulfone, sulfoxide, and thiol.

As generally understood by those of ordinary skill in the art, saturation refers to the state in which all available valence bonds of an atom (e.g., carbon) are attached to other atoms. Similarly, unsaturation refers to the state in which not all the available valence bonds are attached to other atoms; in such compounds the extra bonds usually take the form of double or triple bonds (usually with carbon). For example, a carbon chain is saturated when there are no double or triple bonds present along the chain or directly connected to the chain (e.g., a carbonyl), and is unsaturated when at least one double or triple bond is present along the chain or directly connected to the chain (e.g., a carbonyl). Further, the presence or absence of a substituent depending upon chain saturation will be understood by those of ordinary skill in the art to depend upon the valence requirement of the atom or atoms to which the substituent binds (e.g., carbon).

Alkenyl, as used herein, refers to a straight or branched chain hydrocarbon containing from 2 to 10 or 20 or more carbons, and containing at least one carbon-carbon double bond, formed structurally, for example, by the replacement of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl and the like. Alkenyl groups as described herein are optionally substituted (e.g., from 1 to 3 or 4 times) with substituents independently selected from, but not limited to, H, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocyclo, heteroaryl, hydroxy, nitro, oxo, oxy, peptide, sulfone, sulfoxide, and thiol.

Alkynyl, as used herein, refers to a straight or branched chain hydrocarbon group containing from 2 to 10 or 20 or more carbon atoms, and containing at least one carbon-carbon triple bond. Representative examples of alkynyl include, but are not limited, to acetylenyl, 1-propynyl, 2-propynyl, 1-butyryl, 2-butyryl, 2-pentynyl, and the like. Alkynyl groups as described herein are optionally substituted (e.g., from 1 to 3 or 4 times) with substituents independently selected from, but not limited to, H, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocyclo, heteroaryl, hydroxy, nitro, oxo, oxy, peptide, sulfone, sulfoxide, and thiol.

The term cycloalkyl, as used herein, refers to a saturated or unsaturated cyclic hydrocarbon group containing from 3 to 8 carbons or more. Representative examples of cycloalkyl include cyclopropyl, cyclobutyl, cyclobutenyl, cyclopentyl, cyclohexyl, cycloheptyl, and cyclooctyl. Cycloalkyl groups as described herein are optionally substituted (e.g., from 1 to 3 or 4 times) with substituents independently selected from, but not limited to, H, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocyclo, heteroaryl, hydroxy, nitro, oxo, oxy, peptide, sulfone, sulfoxide, and thiol.

Heterocyclo, heterocyclic, and heterocycle as used herein refer to a monocyclic, bicyclic or tricyclic ring system. Monocyclic heterocycle ring systems are exemplified by any 3, 4, 5 or 6 membered ring containing 1, 2, 3, or 4 heteroatoms independently selected from the group consisting of: O, N, and S. The 5 member ring has from 0 to 2 double bonds, and the 6 member ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiomorpholine sulfoxide, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, pyranopyridine, quinoline, quinolizine, quinoxaline, quinazoline, tetrahydroisoquinoline, tetrahydroquinoline, thiopyranopyridine, and the like. Heterocyclo groups as described herein are optionally substituted (e.g., from 1 to 3 or 4 times) with substituents independently selected from, but not limited to, H, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocyclo, heteroaryl, hydroxy, nitro, oxo, oxy, peptide, sulfone, sulfoxide, and thiol.

Aryl as used herein refers to a ring system having one or more aromatic rings. Representative examples of aryl include azulenyl, indanyl, indenyl, naphthyl, phenyl, tetrahydronaphthyl, and the like. The aryl groups of this invention can be optionally substituted with 1, 2, 3, 4, 5, 6 or 7 substituents independently selected from, but not limited to, H, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocyclo, heteroaryl, hydroxy, nitro, oxo, oxy, peptide, sulfone, sulfoxide, and thiol.

Heteroaryl means a cyclic, aromatic hydrocarbon in which one or more carbon atoms have been replaced with heteroatoms. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, pyranyl, isobenzofuranyl, chromenyl, xanthenyl, indolyl, isoindolyl, indolizinyl, triazolyl, pyridazinyl, indazolyl, purinyl, quinolizinyl, isoquinolinyl, quinolyl, phthalazinyl, naphthyridinyl, quinoxalinyl, isothiazolyl, and benzo[b]thienyl. Preferred heteroaryl groups are five and six membered rings and contain from one to three heteroatoms independently selected from the group consisting of: O, N, and S. The heteroaryl group, including each heteroatom, can be unsubstituted or substituted with from 1 to 4 suitable substituents, as chemically feasible. For example, the heteroatom S may be substituted with one or two oxo groups, which may be shown as =O. Heteroaryl groups as described herein are optionally substituted (e.g., from 1 to 3 or 4 times) with substituents independently selected from, but not limited to, H, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocyclo, heteroaryl, hydroxy, nitro, oxo, oxy, peptide, sulfone, sulfoxide, and thiol.

II. Methods of Making the Compounds

The compounds described herein can be prepared in a variety of ways. The compounds can be synthesized using various synthetic methods. At least some of these methods are known in the art of synthetic organic chemistry. The compounds described herein can be prepared from readily available starting materials. Optimum reaction conditions can vary with the particular reactants or solvent used, but such conditions can be determined by one skilled in the art by routine optimization procedures.

Variations on Formulas I-III include the addition, subtraction, or movement of the various constituents as described for each compound. Similarly, when one or more chiral centers are present in a molecule, all possible chiral variants are included. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts, Greene's Protective Groups in Organic Synthesis, 5th. Ed., Wiley & Sons, 2014, which is incorporated herein by reference in its entirety.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Exemplary methods for synthesizing the compounds as described herein are provided in Example 1 Below.

III. Pharmaceutical Formulations

The compounds described herein or derivatives thereof can be provided in a pharmaceutical composition. The compounds described herein may be suitable for parenteral, oral, inhalation spray, topical, rectal, nasal, buccal, vaginal, or implanted reservoir administration. The term parenteral as used herein includes subcutaneous, intradermal, intravenous, intramuscular, intra-articular, intra-synovial, intrasternal, intrathecal, intrahepatic, intralesional and intracranial injection or infusion techniques. Optionally, the compounds described herein can administered orally, topically, intranasally, intravenously, subcutaneously, intradermally, transdermally, intramucosally, intramuscularly, by inhalation spray, rectally, nasally, sublingually, buccally, vaginally or via an implanted reservoir.

Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the compound described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington: The Science and Practice of Pharmacy, 22d Edition, Loyd et al. eds., Pharmaceutical Press and Philadelphia College of Pharmacy at University of the Sciences (2012). Examples of physiologically acceptable carriers include buffers, such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers, such as polyvinylpyrrolidone; amino acids such as glycine, glutamine, asparagine, arginine or lysine; monosaccharides, disaccharides, and other carbohydrates, including glucose, mannose, or dextrins; chelating agents, such as EDTA; sugar alcohols, such as mannitol or sorbitol; salt-forming counterions, such as sodium; and/or nonionic surfactants, such as TWEEN® (ICI, Inc.; Bridgewater, N.J.), polyethylene glycol (PEG), and PLURONICS™ (BASF; Florham Park, N.J.).

Compositions containing the compound described herein or derivatives thereof suitable for parenteral injection may comprise physiologically acceptable sterile aqueous or non-aqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants, such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof is admixed with at least one inert customary excipient (or carrier), such as sodium citrate or dicalcium phosphate, or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, may contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compounds described herein or derivatives thereof for rectal administrations are optionally suppositories, which can be prepared by mixing the compounds with suitable non-irritating excipients or carriers, such as cocoa butter, polyethyleneglycol or a suppository wax, which are solid at ordinary temperatures but liquid at body temperature and, therefore, melt in the rectum or vaginal cavity and release the active component.

Dosage forms for topical administration of the compounds described herein or derivatives thereof include ointments, powders, sprays, and inhalants. The compounds described herein or derivatives thereof are admixed under sterile conditions with a physiologically acceptable carrier and any preservatives, buffers, or propellants as may be required. Ophthalmic formulations, ointments, powders, and solutions are also contemplated as being within the scope of the compositions.

The compositions can include one or more of the compounds described herein or pharmaceutically acceptable salts thereof. As used herein, the term pharmaceutically acceptable salt refers to those salts of the compound described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See S. M. Barge et al., J. Pharm. Sci. (1977) 66, 1, which is incorporated herein by reference in its entirety, at least, for compositions taught therein.)

Administration of the compounds and compositions described herein or pharmaceutically acceptable salts thereof can be carried out using therapeutically effective amounts of the compounds and compositions described herein or pharmaceutically acceptable salts thereof as described herein for periods of time effective to treat a disorder. The effective amount of the compounds and compositions described herein or pharmaceutically acceptable salts thereof as described herein may be determined by one of ordinary skill in the art and includes exemplary dosage amounts for a mammal of from about 0.5 to about 200 mg/kg of body weight of active compound per day, which may be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day.

Those of skill in the art will understand that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. The precise dose to be employed in the formulation will also depend on the route of administration, and the seriousness of the disease or disorder, and should be decided according to the judgment of the practitioner and each subject's circumstances. Effective doses can be extrapolated from dose-response curves derived from in vitro or animal model test systems. Further, depending on the route of administration, one of skill in the art would know how to determine doses that result in a plasma concentration for a desired level of response in the cells, tissues and/or organs of a subject.

IV. Methods of Use

Provided herein are methods to treat, prevent, or ameliorate metabolic disorders and cancer in a subject. The methods include administering to a subject an effective amount of one or more of the compounds or compositions described herein, or a pharmaceutically acceptable salt or prodrug thereof. The expression "effective amount," when used to describe an amount of compound in a method, refers to the amount of a compound that achieves the desired pharmacological effect or other effect, for example, an amount that results in tumor growth rate reduction. The compounds and compositions described herein or pharmaceutically acceptable salts thereof are useful for treating metabolic disorders and cancer in humans, including, without limitation, pediatric and geriatric populations, and in animals, e.g., veterinary applications.

The methods and compounds as described herein are useful in treating or preventing metabolic diseases. As used herein, metabolic disorder or metabolic disease (wherein disorder and disease can be used interchangeably) refers to a condition caused by an abnormal metabolic process. Common metabolic disorders include, but are not limited to, diabetes, insulin resistance, obesity, dyslipidemia, lypolipedemia, hyperthyroidism, hypothyroidism, galactosemia and phenylketonuria. Diabetes can refer to a disease diagnosed as diabetes according to the diagnostic standard, for example, of WHO (World Health Organization), Japan Diabetes Society, American Diabetes Association or European Association for the Study of Diabetes and includes Type 1 diabetes, Type 2 diabetes, gestational or pregnancy diabetes, and the like. Type 2 diabetes can be characterized by its resistance to the action of insulin, i.e., insulin resistance. Insulin resistance can mean a disease diagnosed as insulin resistance, based on the insulin resistance index (fasting blood sugar (mg/dL)×fasting insulin (microU/mL)÷405) or on the results obtained by examination by glucose clamp method or the like and includes syndrome X additionally. In addition to Type 2 diabetes, diseases with "insulin resistance" include, for example, steatosis/fatty liver, particularly NAFLD (non-alcoholic fatty liver disease), NASH (non-alcoholic steatohepatitis), coronary heart diseases (CHDs), arteriosclerotic diseases, hyperglycemia, lipodosis, impaired glucose tolerance, hypertension, hyperlipemia, diabetes complications, pregnancy diabetes, polycystic ovary syndrome and the like.

The methods for treating or preventing metabolic diseases includes administering to the subject one or more of the compounds or compositions as described herein. Optionally, the method also includes the step of selecting a subject having a metabolic disease.

The compounds described herein have glucose-lowering effects, insulin-sensitizing effects, and/or anti-obesity properties, and can lower plasma triglyceride levels. Thus, the compounds described herein can be used to treat or prevent metabolic disorders, diabetes, insulin resistance, glucose intolerance, obesity, steatosis, and/or inflammation. The methods for treating or preventing metabolic disorders, diabetes, insulin resistance, glucose intolerance, obesity, steatosis, and/or inflammation comprises administering to the subject one or more of the compounds or compositions as described herein. Optionally, the method also includes the step of selecting a subject having a metabolic disorder, diabetes (Type 1 or Type 2), insulin resistance, glucose intolerance, obesity, steatosis, and/or inflammation. In some embodiments, the diabetes is Type 2 (T2DM).

Optionally, the compounds described herein can have cholesterol-lowering effect or a free-fatty acid lowering effect, as compared to a control.

Further provided herein are methods for treating cancer or a benign tumor using the compounds or compositions described herein. Cancer, as used herein, refers to any malignant abnormal growth of cells, and epithelial cancer refers to cancer that typically develops from epithelium or related tissues in the skin, hollow viscera, and other organs. In some embodiments, the epithelial cancer is cancer of the breast, prostate, pancreas, ovary, serous adenocarcinoma of the ovary, fallopian tube, colon, gallbladder, bladder, urethra, stomach, endometrium, bronchus, lung or kidney. Optionally, the cancer is an epithelial cancer. The epithelial cancer can be cancer of the skin or breast.

The methods for treating or preventing cancer or a benign tumor includes administering to the subject one or more of the compounds or compositions as described herein. Optionally, the method also includes the step of selecting a subject having cancer or at risk for developing cancer.

The methods of treating or preventing metabolic disorders or cancer in a subject can further comprise administering to the subject a therapeutic agent or radiation therapy or a combination thereof. Thus, the provided compositions and methods can include one or more additional agents. The one or more additional agents and the compounds described herein or pharmaceutically acceptable salts or prodrugs thereof can be administered in any order, including concomitant, simultaneous, or sequential administration. Sequential administration can be temporally spaced order of up to several days apart. The methods can also include more than a single administration of the one or more additional agents and/or the compounds described herein or pharmaceutically acceptable salts or prodrugs thereof. The administration of the one or more additional agents and the compounds described herein or pharmaceutically acceptable salts or prodrugs thereof can be by the same or different routes and concurrently or sequentially.

Therapeutic agents include, but are not limited to, chemotherapeutic agents, anti-depressants, anxiolytics, antibodies, antivirals, steroidal and non-steroidal anti-inflammatories, conventional immunotherapeutic agents, cytokines, chemokines, and/or growth factors. Therapeutic agents also include insulin and agents (e.g., glyburide, exenatide, pramlinitide, and metformin) used to control blood sugar in subjects with diabetes and anti-obesity medications (e.g., orlistat, sibutramine, and rimonabant).

The therapeutic agent can, for example, be a chemotherapeutic agent. A chemotherapeutic agent is a compound or composition effective in inhibiting or arresting the growth of an abnormally growing cell. Thus, such an agent may be used therapeutically to treat cancer as well as other diseases marked by abnormal cell growth. Illustrative examples of chemotherapeutic compounds include, but are not limited to, antiestrogens (e.g., tamoxifen or fulvestrant) and aromatase inhibitors (e.g., letrozole).

Any of the aforementioned therapeutic agents can be used in any combination with the compositions described herein. Combinations are administered either concomitantly (e.g., as an admixture), separately but simultaneously (e.g., via separate intravenous lines into the same subject), or sequentially (e.g., one of the compounds or agents is given first followed by the second). Thus, the term combination is used to refer to concomitant, simultaneous, or sequential administration of two or more agents.

The methods and compounds as described herein are useful for both prophylactic and therapeutic treatment. For prophylactic use, a therapeutically effective amount of the compounds and compositions or pharmaceutically acceptable salts thereof as described herein are administered to a subject prior to onset (e.g., before obvious signs of metabolic disorders or cancer), during early onset (e.g., upon initial signs and symptoms of metabolic disorders or cancer), or after the development of metabolic disorders or cancer. Prophylactic administration can occur for several days to years prior to the manifestation of symptoms of metabolic disorders and cancer. Therapeutic treatment involves administering to a subject a therapeutically effective amount of the compounds and compositions or pharmaceutically acceptable salts thereof as described herein after metabolic disorders and cancer is diagnosed.

The methods herein for prophylactic and therapeutic treatment optionally comprise selecting a subject with or at risk of developing a metabolic disorder or cancer. A skilled artisan can make such a determination using, for example, a variety of prognostic and diagnostic methods, including, for example, a personal or family history of the disease or condition, clinical tests (e.g., imaging, biopsy, genetic tests and the like for cancer; measurements of body weight or body fat for obesity and diabetes; blood glucose levels for diabetes), and the like.

Optionally, the subject for the methods described herein is a rodent. Optionally, the subject is human. The subject is optionally obese or morbidly obese. The subject can be pre-diabetic or diabetic.

Optionally, the compounds described herein do not cause adverse effects that are often associated with other rexinoids, such as elevation of serum triglyceride levels, hepatomegaly, and an alteration of the thyroid hormone axis.

V. Kits

Also provided herein are kits for treating or preventing metabolic disorders, diabetes, insulin resistance, glucose intolerance, obesity, steatosis, inflammation, or cancer in a subject. A kit can include any of the compounds described herein or a pharmaceutically acceptable salt or prodrug thereof. For example, a kit can include one or more compounds of Formula I, Formula II, Formula III, or combinations thereof. A kit can further include one or more additional agents, such as an anti-inflammatory agent or a chemotherapeutic agent. A kit can include an oral formulation of any of the compounds or compositions described herein. A kit can additionally include directions for use of the kit (e.g., instructions for treating a subject), a container, a means for administering the compounds or compositions, and/or a carrier. Kits can include multiple doses (e.g., in a blister pack), can include means for administration (e.g., a delivery device like a syringe) or the like.

As used herein the terms treatment, treat, or treating refer to a method of reducing one or more symptoms of a disease or condition. Thus in the disclosed method, treatment can refer to a 10%, 20%, 30%, 40%, 50%, 60%, 70%, 80%, 90%, or 100% reduction in the severity of one or more symptoms of the disease or condition. For example, a method for treating a disease is considered to be a treatment if there is a 10% reduction in one or more symptoms or signs (e.g., size of the tumor or rate of tumor growth) of the disease in a subject as compared to a control. As used herein, control refers to the untreated condition (e.g., the tumor cells not treated with the compounds and compositions described herein). Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refer to an action, for example, administration of a composition or therapeutic agent, that occurs before or at about the same time a subject begins to show one or more symptoms of the disease or disorder, which inhibits or delays onset or severity of one or more symptoms of the disease or disorder.

As used herein, references to decreasing, reducing, or inhibiting include a change of 10%, 20%, 30%, 40%, 50%, 60%, 70%, 80%, 90%, or greater as compared to a control level. Such terms can include, but do not necessarily include, complete elimination.

As used herein, references to lowering effects (e.g., glucose-lowering effect, triglyceride-lowering effect, cholesterol-lowering effect, and free-fatty acid-lowering effect) and sensitizing effects (e.g., insulin-sensitizing effects) include a change of 10%, 20%, 30%, 40%, 50%, 60%, 70%, 80%, 90%, or greater as compared to a control level. Such terms can include, but do not necessarily include, achieving a normal amount in a subject. As used herein, normal amount refers to an amount that is able to produce a normal physiological or molecular response in a subject and can vary from one subject to another.

As used herein, subject means both mammals and non-mammals. Mammals include, for example, humans; non-human primates, e.g., apes and monkeys; cattle; horses; sheep; rodents (e.g., rats and mice); pigs; and goats. Non-mammals include, for example, fish and birds.

Throughout this application, various publications are referenced. The disclosures of these publications in their entireties are hereby incorporated by reference into this application.

The examples below are intended to further illustrate certain aspects of the methods and compounds described herein, and are not intended to limit the scope of the claims.

EXAMPLES

Example 1: Synthesis of Retinoid X Receptor (RXR) Selective Agonists and Agents

Synthesis of 5-(3-(1-naphthyl)phenyl)-3-methylpenta-2,4-dienoic Acid 5 (UAB119; Compound 4): As depicted in Scheme 1, compound 5 was synthesized in three steps starting from naphthalene-1-boronic acid 1 utilizing Suzuki reaction conditions. Coupling of boronic acid 1 with m-bromobenzaldehyde 2 in the presence of tetrakis-(triphenylphosphine)palladium gave the desired aldehyde 3 in 70% yield after purification by chromatography. The aldehyde 3 was then subjected to Horner-Emmons reaction conditions in the presence of triethylphosphonosenecioate and base to give the desired ester 4 as a 9:1 mixture of 4E, 2E and 4E, 2Z isomers. While the cis-trans isomers were not separable at this stage, ester 4 was purified by column chromatography. Ester 4 was then hydrolyzed under basic conditions to give the acid 5 as a mixture of isomers. The desired isomer 4E, 2E-5 was then obtained by selective crystallization.

Scheme 1: Synthesis of 5-(3-(1-Naphthyl)phenyl)-3-methylpenta-2,4-dienoic Acid Isomers

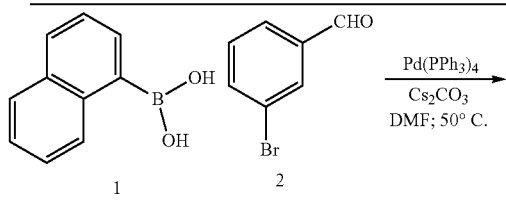

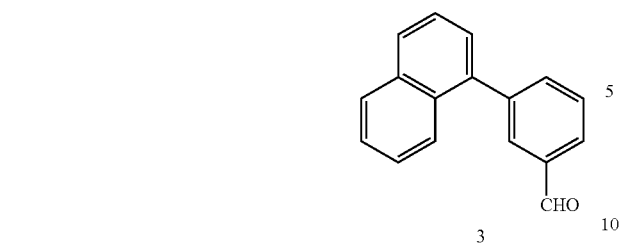

3

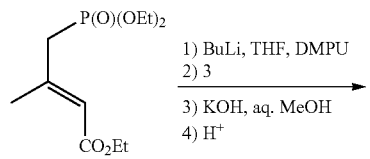

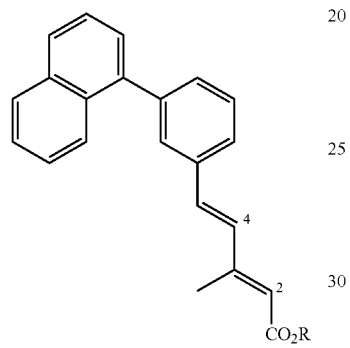

4: R = Et
5: R = H; UAB 119

Synthesis of 5-(4-(1-naphthyl)phenyl)-3-methylpenta-2,4-dienoic Acid 9 (UAB118; Compound 3): As depicted in Scheme 2, compound 9 was synthesized in three steps starting from naphthalene-1-boronic acid 1 utilizing Suzuki reaction conditions. Coupling of boronic acid 1 with p-bromobenzaldehyde 6 in the presence of tetrakis-(triphenylphosphine)palladium gave the desired aldehyde 7 in 70% yield after purification by chromatography. The aldehyde 7 was then subjected to Horner-Emmons reaction conditions in the presence of triethylphosphonosenecioate and base to give the desired ester 8 as a 9:1 mixture of 4E, 2E and 4E, 2Z isomers. While the cis-trans isomers were not separable at this stage, ester 8 was purified by column chromatography. Ester 8 was then hydrolyzed under basic conditions to give the acid 9 as a mixture of isomers. The desired isomer 4E, 2E-9 was then obtained by selective crystallization.

Scheme 2. Synthesis of 5-(4-(1-Naphthyl)phenyl)-3-methylpenta-2,4-dienoic Acid Isomers

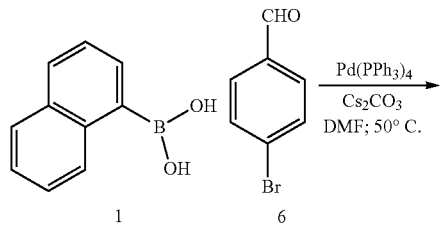

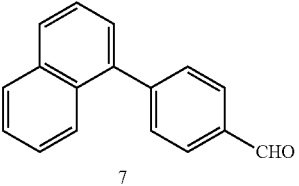

7

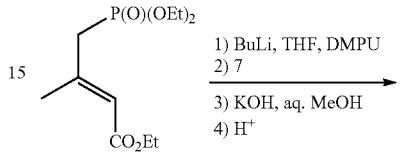

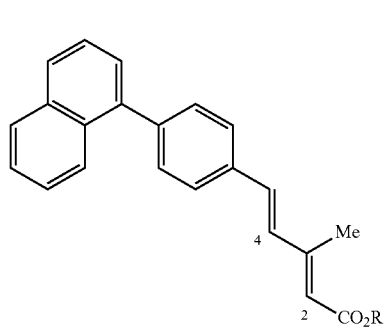

8: R = Et
9: R = H; UAB 118

Synthesis of 3-(3-(1-Naphthyl)phenyl)propenoic Acids 10 (UAB122; Compound 1) and 10a (UAB125; Compound 10): As depicted in Scheme 3, the syntheses of 3-(3-(1-naphthyl)phenyl)propenoic acid 10 and 3-(3-(4-methyl-1-naphthyl)phenyl)propenoic acid 10a were accomplished utilizing Knoevenagel condensation conditions. A solution of the appropriate aldehyde, 3 or 3a, in pyridine was heated at reflux in the presence of malonic acid and piperidine. Following the completion of the reaction, the mixture was acidified to give the target product, 10 or 10a, as a single isomer.

Scheme 3. Synthesis of 3-(3-(1-Naphthyl)phenyl)propenoic Acids

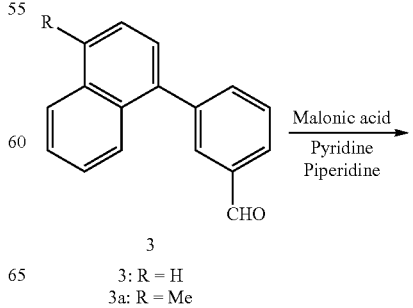

3: R = H
3a: R = Me

-continued

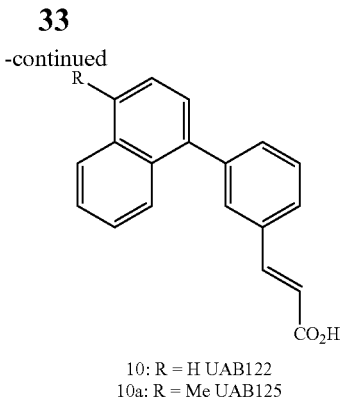

10: R = H UAB122
10a: R = Me UAB125

Synthesis of 3-(4-(1-Naphthyl)phenyl)propenoic Acid 11 (UAB126; Compound 2): As depicted in Scheme 4, the synthesis of 3-(4-(1-naphthyl)phenyl)propenoic acid 11 was accomplished utilizing Knoevenagel condensation conditions. A solution of the appropriate aldehyde, 7, in pyridine was heated at reflux in the presence of malonic acid and piperidine. Following the completion of the reaction, the mixture was acidified to give the target product, 11, as a single isomer.

Scheme 4. Synthesis of 3-(4-(1-Naphthyl)phenyl)propenoic Acid

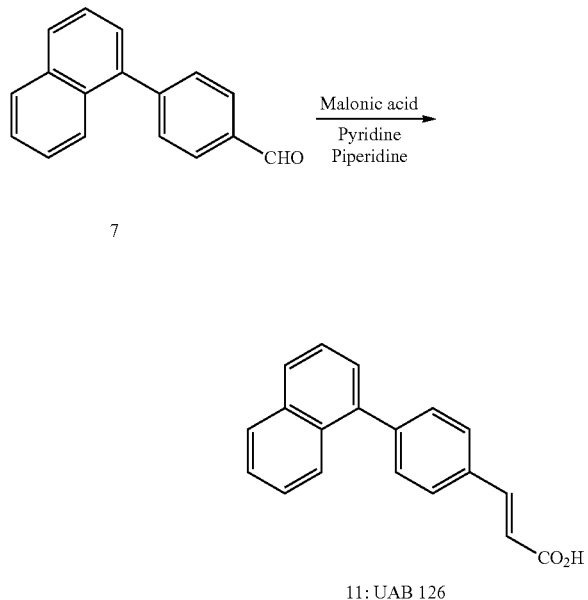

11: UAB 126

As depicted in Scheme 5, the target compounds 14 (UAB123; Compound 8) and 15 (UAB 121; Compound 6) were each synthesized in a single step following the Suzuki coupling of the naphthaleneboronic acid 1 with the appropriate bromo-substituted aryl acid 12 or 13 to provide the rexinoids 14 and 15. Compounds 14 and 15 were each obtained in 70-75% yields after purification by column chromatography.

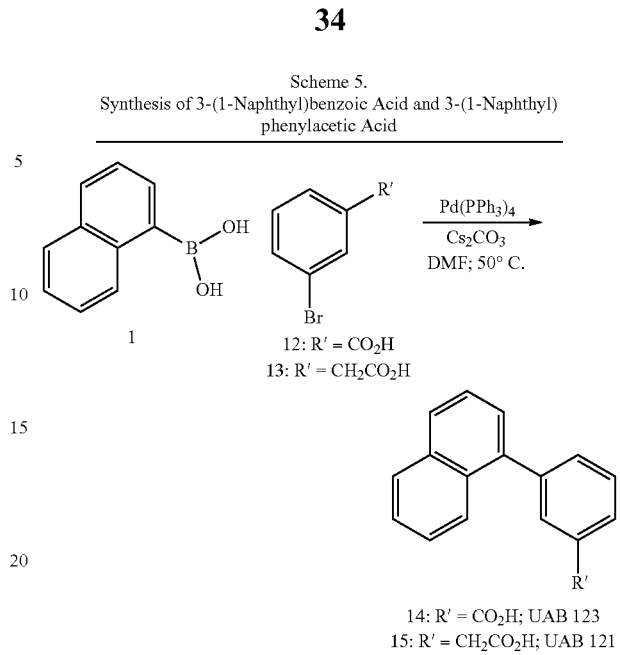

Scheme 5.
Synthesis of 3-(1-Naphthyl)benzoic Acid and 3-(1-Naphthyl) phenylacetic Acid

12: R' = $CO_2H$
13: R' = $CH_2CO_2H$

14: R' = $CO_2H$; UAB 123
15: R' = $CH_2CO_2H$; UAB 121

Similar synthetic methodologies as shown in Schemes 1-5 can be used to synthesize the rexinoid compounds described herein.

Example 2: Efficacy of Rexinoids on Mammary Cancers

Mammary carcinogenesis was induced in female, transgenic erbB2$^{+/-}$ mice using 7,12-Dimethylbenz[a]anthracene (DMBA). The mice were orally administered 9-cis-UAB30 (a tissue selective rexinoid), TARGRETIN® (Valeant Pharmaceuticals, West Laurel, Calif.) (i.e., bexarotene, which is a potent RXR agonist), UAB125, or UAB126. The control mice were not administered any compounds. As shown in FIG. 1, the retinoid compounds described herein were found to be effective (>70%) in the prevention of ER-negative mammary carcinogenesis in transgenic mice. Specifically, UAB125 and UAB126 prevented the formation of 68% and 79%, respectively, of the estrogen-negative mammary cancers, while 9-cis-UAB30 and TARGRETIN® prevented only 54% and 65%, respectively.

Figure 2:
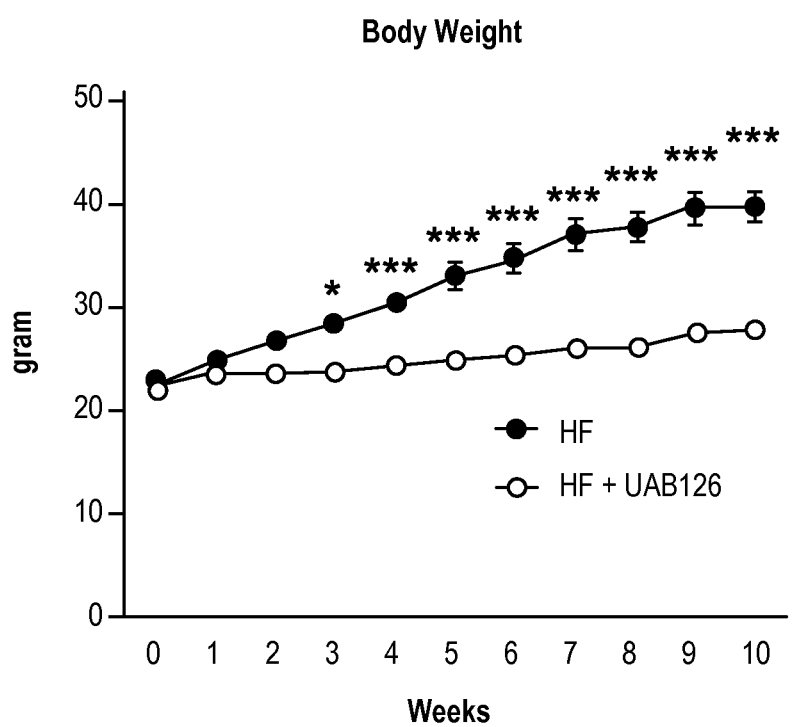
FIG. 2 is a graph showing the body weight of mice on a high fat diet without treatment (HF) and with treatment using Compound UAB126 (HF+UAB126).

Example 3: Treatment with Compound UAB126 Prevented High Fat Diet-Induced Obesity Twelve C57BL/6J mice were randomly divided into two groups, namely high fat diet (HFD) (60% of calories from fat) fed with or without Compound UAB126 (1.5 g/kg food) for 10 weeks. As shown in FIG. 2, HFD fed mice treated with Compound UAB126 (labeled as "HF+UAB126" in FIG. 2) gained less body weight (avg. initial 22.5 g, and final 27.8 g), compared to HFD fed mice treated without Compound UAB126 (labeled as "HF" in FIG. 2) (avg. initial 23 g, and final 40 g).

Figure 3:
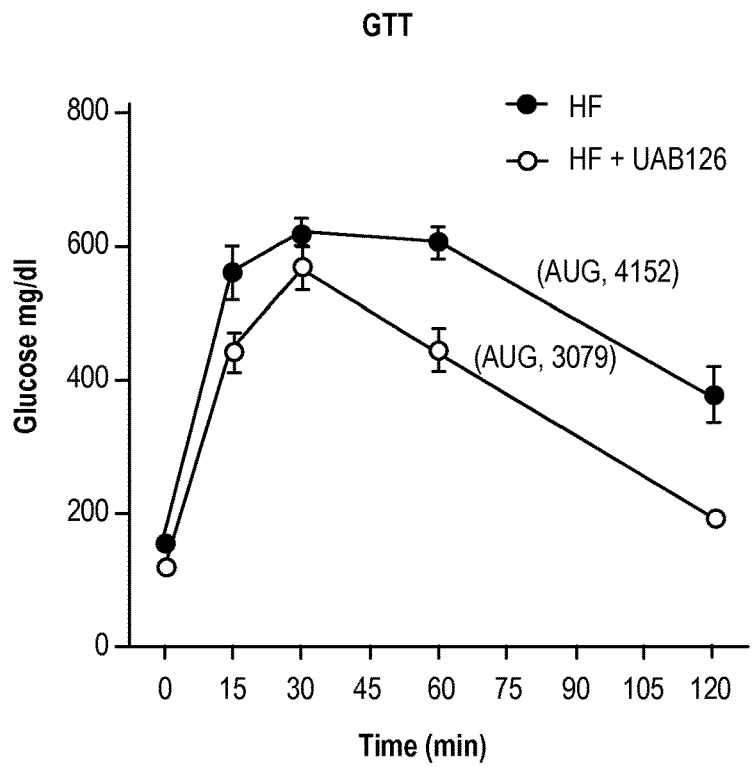
FIG. 3 is a graph showing the glucose tolerance of mice over time on a high fat diet without treatment (HF) and with treatment using Compound UAB126 (HF+UAB126).
Figure 4:
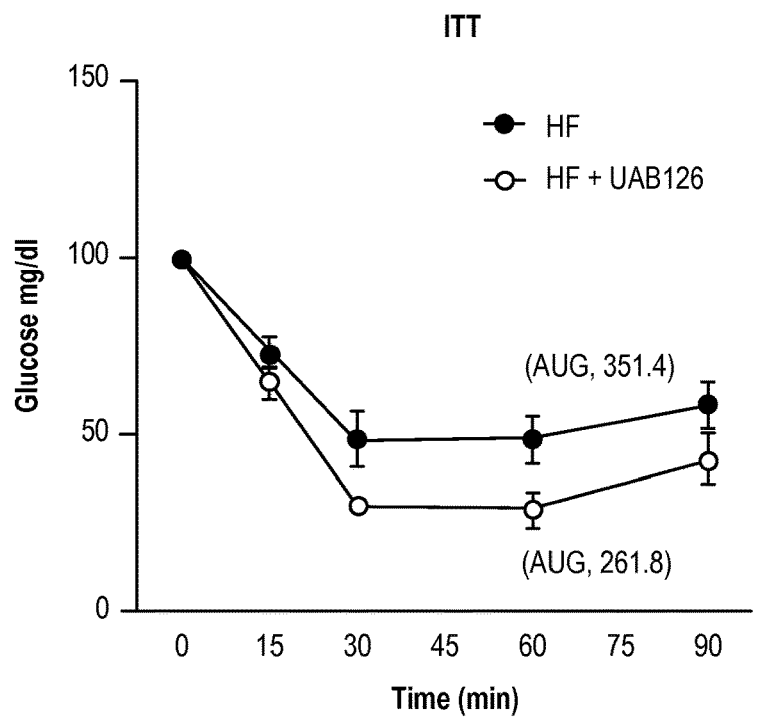
FIG. 4 is a graph showing the insulin sensitivity of mice over time on a high fat diet without treatment (HF) and with treatment using Compound UAB126 (HF+UAB126).

Example 4: Treatment with Compound UAB126 Improved Glucose Tolerance and Insulin Sensitivity The mice fed a high fat diet (HFD) with Compound UAB126 were more glucose tolerant and insulin sensitive than the mice fed HFD alone (FIGS. 3 and 4). Also, fasting glucose levels in mice fed HFD with Compound UAB126 were lower than mice fed HFD (FIG. 5). Body composition was measured by quantitative magnetic resonance (QMR), as shown in FIG. 6. Fat mass was markedly reduced, while lean mass was also slightly reduced, following Compound UAB126 treatment. When body composition was normalized by body weight, there was more lean mass and less fat mass in Compound UAB126 treated mice compared to HFD fed mice (FIG. 6B; see FIG. 6A for comparison without normalization). Food intake was not different between the 2 groups. These data show that Compound UAB126 has effects on energy balance.

Example 5: Treatment with Compound UAB126 Reduced Serum Triglyceride Levels

Figure 7:
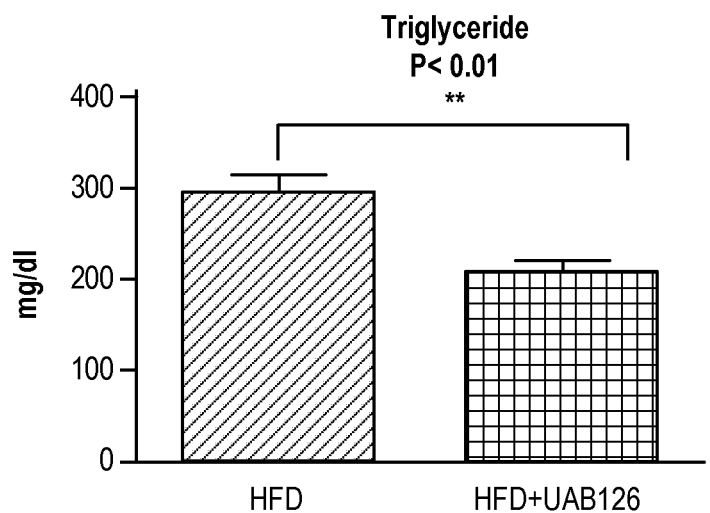
FIG. 7 is a graph showing the triglyceride levels of mice on a high fat diet without treatment (HF) and with treatment using Compound UAB126 (HF+UAB126).
Figure 8A:
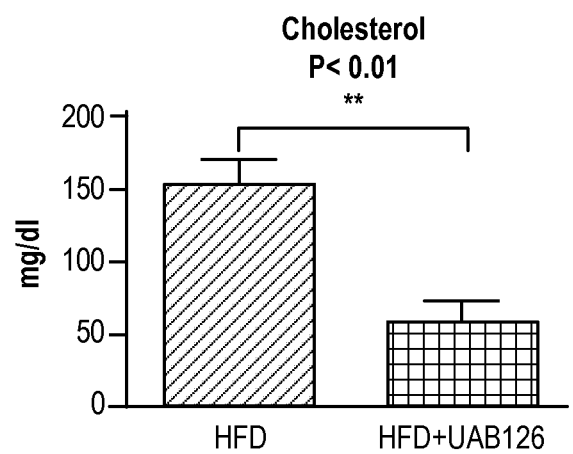
FIG. 8A is a graph showing the serum cholesterol of mice on a high fat diet without treatment (HF) and with treatment using Compound UAB126 (HF+UAB126).
Figure 8B:
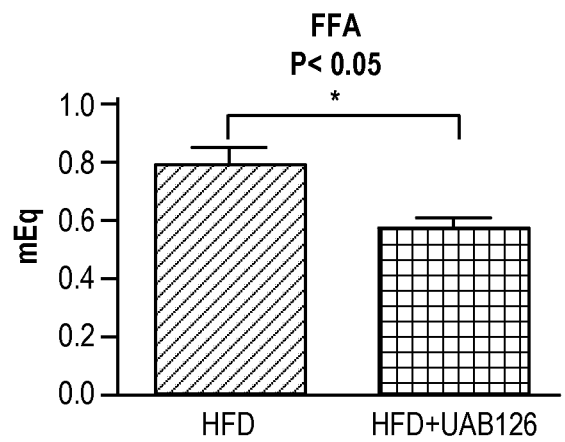
FIG. 8B is a graph showing the free fatty acids (FFA) of mice on a high fat diet without treatment (HF) and with treatment using Compound UAB126 (HF+UAB126).

Previously developed rexinoids have the adverse side effect of elevating serum triglyceride (TG) level. In contrast, treatment with Compound UAB126 significantly reduced triglyceride levels (FIG. 7). Furthermore, Compound UAB126 treated mice show significantly decreased cholesterol (FIG. 8A) and free fatty acids (FFA; FIG. 8B) in the serum compared to HFD vehicle treated mice. Thus, Compound UAB126 can regulate lipid metabolism.

Example 6: Effect of Compound UAB126 on Metabolism on Whole Body and Tissue Specific Energy Metabolism Twenty-four C57BL/6J mice are divided into four groups (6/group); namely, mice fed normal chow (10% fat from total calorie) or high fat (60% fat from total calorie) diets for 12 weeks, with and without Compound UAB126 (1.5 g/kg food). The following parameters are evaluated.

A. Whole body parameters: Food intake, energy expenditure, and physical activity are measured through the use of metabolic cages. Glucose, insulin, and pyruvate tolerance tests are conducted. Fasting plasma, glucose, insulin, leptin, and adiponectin levels are measured. Lipid profiles (triglyceride, cholesterol, nonesterified fatty acids) and pro-inflammatory cytokine (Tnf-α, IL-1α, CRP and IL-6) levels are measured. Because other rexinoids also alter thyroid hormone levels, mouse TSH, free T3 and T4 levels in the serum are measured.

B. Tissue specific parameters: Macrophage infiltration of adipose tissue is a hallmark of obesity-related inflammation. Macrophage infiltration in adipose tissue and the size of adipocytes are examined. Liver, skeletal muscle, and adipose tissue are isolated from mice following an acute insulin challenge, after which, the phosphorylation status of insulin signaling components (e.g., IR, IRS-1, Akt) are examined. Glucose uptake in the skeletal muscle with and without insulin ex vivo is measured. Expression of gluconeogenic and lipogenic enzymes, and lipid contents in the liver are evaluated. Also, expression of adipokines, including adiponectin, resistin, and leptin are examined. With isolated tissues, histological analysis is performed by observing the size of adipocytes and macrophage infiltration in adipose tissue. Hepatic tissues are stained with oil red O staining (indication of steatosis). Genomic profiles in liver, adipose tissue, and skeletal muscle are examined by using Affymetrix GeneChip mouse array (UAB genomics core facility). RT-PCR validation focuses on genes involved in gluconeogenesis, lipogenesis, and lipolysis.

Example 7: Molecular Mechanisms for Mediating the Metabolic Effects of Compound UAB126

To understand the molecular mechanisms by which Compound UAB126 influences insulin sensitivity, a cell based system is utilized (i.e., HepG2 cells, a human hepatocyte cell line, and mouse primary hepatocytes). In some cases, siRNA is administered to confirm the results after identifying a nuclear receptor (NR) partner(s).

A. NR identification: To identify nuclear receptors (NR) that are activated by Compound UAB126, luciferase constructs are used. HepG2 cells are transfected with luciferase constructs containing the responsive elements of various NRs with pRL-tk (internal control for transfection normalization). To compare the potency of RXR agonists, the luciferase activity of Compound UAB126 is compared to those of TARGRETIN® (a potent RXR agonist) and 9cUAB30 (a tissue-selective rexinoid).

B. Chip Assays: To examine the direct binding of nuclear receptors, Chip assay is employed by examining promoters of various genes involved in lipid metabolism (SCD1, SREBP1/2, FAS) and oxidative stress (NQO1,CYP1a1, HO-1). The results are verified through real time qPCR analysis.

C. Insulin signaling pathways: To examine the direct effect of Compound UAB126 on insulin signaling, the ability of Compound UAB126 to activate insulin signaling molecules, including, pIR, pIRS-1, and pAkt, is determined. In some cases, an improvement of Compound UAB126 on insulin signaling following TNF-α or palmitate treatment is determined.

D. Lipid metabolism: Hepatic TG synthesis and de novo lipogenesis are measured by using [1,2-14C]-acetate and [1-14C]-palmitate, respectively, with and without Compound UAB126. Concurrently, the expression of proteins that are involved in lipogenesis after cells are treated with palmitate with and without Compound UAB126 are examined.

E. Fatty acid oxidation (FAO): Fatty acid oxidation in skeletal muscle and liver can be affected by Compound UAB126. Skeletal muscle and liver are isolated and subjected to fatty acid oxidation.

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods are intended to fall within the scope of the appended claims. Thus, a combination of steps, elements, components, or constituents can be explicitly mentioned herein; however, all other combinations of steps, elements, components, and constituents are included, even though not explicitly stated.

What is claimed is:

1. A method of ameliorating diabetes, dyslipidemia, insulin resistance, glucose intolerance, obesity, or steatosis in a subject, comprising administering to a subject an effective amount of a compound of the following formula:

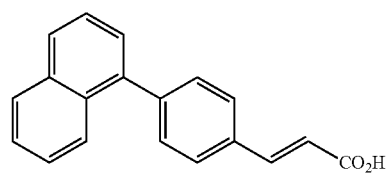 [SMILES: O=C(O)/C=C/c1ccc(-c2cccc3ccccc23)cc1]

or a pharmaceutically acceptable salt thereof.

2. The method of claim 1, wherein administering the compound provides a glucose-lowering effect, an insulin-sensitizing effect, or a plasma triglyceride lowering effect.

3. The method of claim 1, wherein the subject is a rodent or human, obese, morbidly obese, pre-diabetic, or diabetic.

4. The method of claim 1, wherein the compound is administered orally, topically, intranasally, intravenously, subcutaneously, intradermally, transdermally intramucosally intramuscularly, by inhalation spray, rectally, nasally, sublingually, buccally, vaginally or via an implanted reservoir.

5. A method of ameliorating breast cancer in a subject, comprising administering to a subject an effective amount of a compound of the following formula:

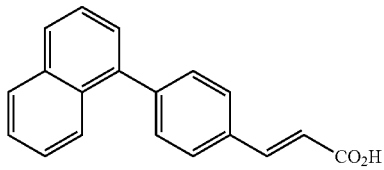 [SMILES: O=C(O)/C=C/c1ccc(-c2cccc3ccccc23)cc1]

or a pharmaceutically acceptable salt thereof.

6. The method of claim 5, wherein the subject is a rodent or human.

7. The method of claim 5, wherein the compound is administered orally, topically, intranasally, intravenously, subcutaneously, intradermally, transdermally intramucosally intramuscularly, by inhalation spray, rectally, nasally, sublingually, buccally, vaginally or via an implanted reservoir.

8. A compound having the following formula:

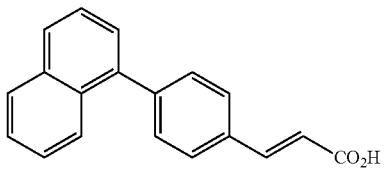

or a pharmaceutically acceptable salt thereof.

* * * * *